United States Patent [19]

Goto et al.

[11] Patent Number: 5,650,374
[45] Date of Patent: Jul. 22, 1997

[54] HERBICIDAL 1-CYCLOPROPYL TETRAZOLINONES

[75] Inventors: Toshio Goto; Yoshinori Kitagawa, both of Tochigi; Seishi Ito, Oyama; Katsuhiko Shibuya, Tochigi; Kazuhiro Ukawa, Oyama; Yoshiko Kyo, Tochigi, all of Japan

[73] Assignee: Nihon Bayer Agrochem K.K., Tokyo, Japan

[21] Appl. No.: 553,160

[22] Filed: Nov. 7, 1995

[30] Foreign Application Priority Data

Nov. 18, 1994 [JP] Japan .................. 6-308385
Apr. 20, 1995 [JP] Japan .................. 7-117634

[51] Int. Cl.⁶ .............. C07D 401/06; C07D 257/04; A01N 43/713; A01N 43/72
[52] U.S. Cl. .............. 507/130; 507/139; 546/165; 546/168; 548/251
[58] Field of Search ............ 548/251; 507/139, 507/130; 546/165, 168

[56] References Cited

U.S. PATENT DOCUMENTS

| | | | |
|---|---|---|---|
| 4,167,574 | 9/1979 | Janssens | 424/267 |
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 4,956,469 | 9/1990 | Covey et al. | 71/92 |
| 5,003,075 | 3/1991 | Covey et al. | 71/92 |
| 5,019,152 | 5/1991 | Covet et al. | 71/92 |
| 5,120,346 | 6/1992 | Covey et al. | 71/92 |
| 5,342,954 | 8/1994 | Goto et al. | 548/251 |
| 5,344,814 | 9/1994 | Goto et al. | 504/261 |
| 5,347,009 | 9/1994 | Goto et al. | 71/92 |
| 5,347,010 | 9/1994 | Goto et al. | 548/251 |
| 5,362,704 | 11/1994 | Goto et al. | 504/134 |

FOREIGN PATENT DOCUMENTS

| | | |
|---|---|---|
| 0146279 | 6/1985 | European Pat. Off. . |
| 0675110A1 | 3/1995 | European Pat. Off. . |
| 0646577 | 4/1995 | European Pat. Off. . |
| 2819873 | 11/1978 | Germany . |

*Primary Examiner*—David B. Springer
*Attorney, Agent, or Firm*—Sprung Horn Kramer & Woods

[57] ABSTRACT

Herbicidal 1-cyclopropyl tetrazolinones of the formula

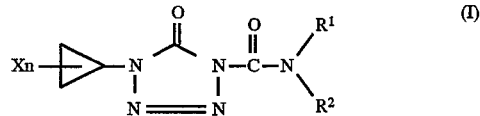

wherein

X represents $C_{1-3}$ alkyl, $C_{2-4}$ alkenyl or halogen, n represents 0 to 5, $R^1$ and $R^2$ each independently represents $C_{1-6}$ alkyl, $C_{2-6}$ alkenyl, $C_{2-6}$ alkynyl, $C_{3-7}$ cycloalkyl which may optionally be substituted by $C_{1-3}$ alkyl, epoxy-$C_{3-5}$ alkan-1-yl, phenyl which may optionally be substituted, or aralkyl which may optionally be substituted, or $R^1$ and $R^2$ together with the N-atom to which they are attached, represent a cyclic ring which may be substituted, and some novel intermediates therefor.

6 Claims, No Drawings

HERBICIDAL 1-CYCLOPROPYL TETRAZOLINONES

The present invention relates to novel 1-cyclopropyl-tetrazolinones, to a process for their preparation, to their use as herbicides, as well as to novel intermediates for their preparation and to processes for the preparation of such intermediates.

It is known that certain substituted tetrazolinones have herbicidal activities (see: U.S. Pat. Nos. 4,618,365 (=EP-A-146,279); 4,826,529; 4,830,661; 4,956,469; 5,003,075; 5,019,152; 5,120,346; 5,342,954; 5,344,814; 5,347,009; 5,347,010 and 5,362,704.

However, the tetrazolinones of the prior art have not been fully satisfactory, especially in respect of their herbicidal efficacy and/or their phytotoxicity against crops.

There have now been found novel 1-cyclopropyl-tetrazolinones represented by the following formula (I),

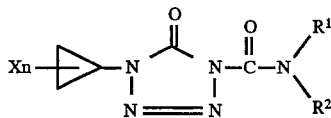

(I)

wherein

X represents $C_{1-3}$ alkyl, $C_{2-4}$ alkenyl or halogen, n represents 0 to 5, and $R^1$ and $R^2$ each independently represents $C_{1-6}$ alkyl, $C_{2-6}$ alkenyl, $C_{2-6}$ alkynyl, $C_{3-7}$ cycloalkyl which may optionally be substituted by $C_{1-3}$ alkyl, epoxy-$C_{3-5}$ alkan-1-yl, phenyl which may optionally be substituted, or aralkyl which may optionally be substituted, or $R^1$ and $R^2$ together with the N-atom to which they are attached represent a ring which may be substituted.

The compounds of formula (I) according to the present invention cab be produced, for example, by the reaction of a compound of the formula

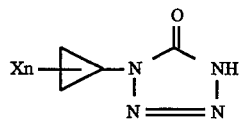

(II)

wherein

X and n are as defined above, with a compound represented by the formula

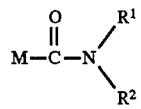

(III)

wherein $R^1$ and $R^2$ are as defined above and

M represents a leaving group such as chlorine, bromine and the like (production method a)).

The compounds of formula (I) according to the present invention have strong herbicidal activity and exhibit herbicidal function and effect which is superior to that of, in particular, the known compounds described in the above-cited EP-A-146,279 which are somewhat similar to the compounds of instant formula (I) as well as very good tolerance by crops.

In this specification, "halogen" comprises fluorine, chlorine, bromine and iodine, preferably fluorine, chlorine or bromine.

Also, "alkyl", "alkenyl", "alkynyl", "cycloalkyl" and "alkan-1-yl" are respectively a saturated, unsaturated or cyclic ring aliphatic hydrocarbon group having the prescribed number of carbon atoms which may optionally have a branched chain.

"Aralkyl" comprises benzyl, 1-phenylethyl and 2-phenylethyl preferably benzyl.

Optional substituents on phenyl and aralkyl include preferably one or two of halogen, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ haloalkylthio, cyano, nitro, $C_{1-4}$ alkylcarbonyl, $C_{1-4}$ alkoxycarbonyl, and/or alkoxyimino-$C_{1-2}$-alkyl, or the like.

The "cyclic ring formed together with the N-atom which may optionally be substituted" is a 5- or 6-membered monocyclic ring containing at least one, preferably only one, N-atom, or a benzo-condensed polycyclic ring such as pyrrolidin-1-yl, indol-1-yl, indolin-1-yl, 1,2-dihydroquinolin-1-yl, 1,2,3,4-tetrahydroquinolin-1-yl, and the like. These rings may optionally be substituted by alkyl such as methyl, ethyl and the like, preference methyl.

Advantageously in compounds of formula (I)

X represents methyl, ethyl, vinyl, allyl, 1-propenyl, fluorine, chlorine, or bromine, n represents 0 to 4, and $R^1$ and $R^2$ each independently represents $C_{1-4}$ alkyl, $C_{3-5}$ alkenyl, $C_{3-5}$ alkynyl, $C_{3-6}$ cycloalkyl which may optionally be substituted by methyl, 2,3-epoxypropan-1-yl, phenyl which may optionally be substituted or benzyl which may optionally be substituted, the optional substituents on said phenyl or said benzyl being independently selected from the group consisting of halogen, $C_{1-4}$ alkyl, $C_{1-4}$ alkoxy, $C_{1-2}$ haloalkyl, $C_{1-2}$ haloalkoxy, $C_{1-4}$ alkylthio, $C_{1-2}$ haloalkylthio, cyano, nitro, $C_{1-2}$ alkyl-carbonyl and $C_{1-2}$ alkoxy-imino-$C_{1-2}$ alkyl, or $R^1$ and $R^2$ together with the N-atom to which they are attached represent pyrrolidin-1-yl, indol-1-yl, indolin-1-yl, 1,2-dihydroquinolin-1-yl or 1,2,3,4-tetrahydroquinolin-1-yl which may optionally be substituted by methyl.

Preferably in compounds of formula (I)

X represents methyl, ethyl, fluorine or chlorine, n represents 0 to 4, and $R^1$ and $R^2$ each independently represents $C_{1-3}$ alkyl, $C_{3-4}$ alkenyl, $C_{3-5}$ alkynyl, cyclopropyl, cyclopentyl, cyclohexyl which may optionally be substituted by methyl, 2,3-epoxypropan-1-yl, phenyl which may optionally be substituted or benzyl which may optionally be substituted, the optional substituents on said phenyl or said benzyl being independently selected from the group consisting of fluorine, chlorine, bromine, methyl, ethyl, methoxy, ethoxy, difluoromethyl, trifluoromethyl, difluoromethoxy, trifluoromethoxy, methylthio, ethylthio, trifluoromethylthio, cyano, nitro, acetyl, propionyl and 1-methoxyiminoethyl, or $R^1$ and $R^2$ together with the N-atom to which they are attached represent pyrrolidine-1-yl, indol-1-yl, indolin-1-yl, 1,2-dihydroquinolin-1-yl or 1,2,3,4-tetrahydroquinolin-1-yl which may optionally be substituted by methyl.

A process for producing the above-mentioned compounds of formula (I) is illustrated by, the following reaction scheme when 1-cyclopropyl-5(4H)-tetrazolinone and diethyl carbamoyl chloride are used as the starting materials:

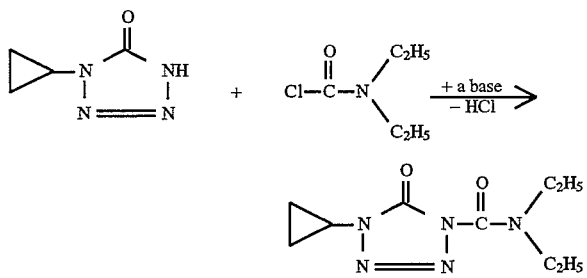

The compounds of formula (II) include new compounds of the formula (II'):

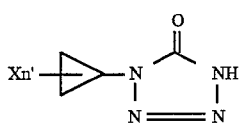

wherein

X is as defined above, and n' represents 1 to 5.

The compounds of formula (II), embracing formula (II'), can be produced by, for instance, a process in which:

b) a compound represented by the formula

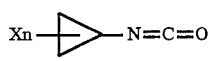

wherein

X and n are as defined above, is reacted with trimethyl silyl azide in the presence of a catalytic amount of boron trifluoride ethyl etherate, c) a compound of above formula (IV) is reacted with sodium azide in a polar solvent in the presence of a catalytic amount of aluminum chloride, d) a compound represented by the formula

wherein

X and n are as defined above, is reacted with trimethyl silyl azide, or e) a compound represented by the formula

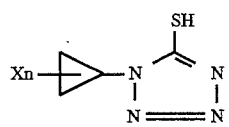

wherein

X and n are as defined above, is reacted with a compound of the formula

wherein

R³ represents hydrogen or methyl.

In the above processes b) and c), the compounds of formula (IV) used as starting materials include known isocyantes and can be produced, for example, by the method described in Chem. Ber., Vol. 106, pp. 3753–3764 (1973), that is, the reaction of diphenyl dichlorosilane with sodium azide to obtain diphenyl diazido silane which is then reacted with cyclopropane-carbonyl chloride of above formula (V), or by the method described in Chem. Ber., Vol. 106, pp. 3765–3768 (1973), that is, by way of cyclopropane carbonyl azide which is prepared by the reaction of a corresponding cyclopropane carboxylic acid ester with trimethyl silyl azide.

The compounds of formula (V) used as starting materials in above process d) comprise acid chlorides and can be easily obtained, for example, by the method described in Japanese Patent Application Laid-Open Publication Kokai Hei 2-88535, that is, by reacting cyclopropane carboxylic acids represented by the formula

wherein

X and n are as defined above, with thionyl chloride as a halogenating agent.

Further, the compounds of above formula (VIII) can be easily obtained for example by reacting vinyl cyclopropanes represented by the formula

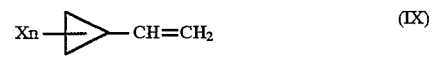

wherein

X and n are as defined above, with potassium permanganate as the oxidizing agent.

The vinyl cyclopropanes of above formula (IX) are obtained, for example, by the methods described in Liebigs Ann. Chem., Vol. 710, pp. 17–35 (1967) and Chem. Ber., Vol. 109, pp.2351–2369(1976).

Also, the compounds of formula (VIII) are easily obtained by hydrolysis of the corresponding cyclopropane carboxylic acid esters. Such cyclopropane carboxylic acid esters can be produced by any known method such as, e.g., reaction of a diazoacetic acid ester with an olefin described in Comprehensive Organic Synthesis (1991), Vol. 4, p. 1031 (Pergamon Press); reaction by thermolysis or photolysis of, e.g., 1-pyrazoline carboxylic acid ester described in the same article, pp. 953–960; an additional reaction of an α,β-unsaturated ester with carbene described in Shin-Jikken Kagaku Koza (New Lecture Course of Experimental Chemistry), Vol. 14, p. 86 (Maruzen); a cyclizing reaction of a Y-haloester by way of a carbanion described in Shin-Jikken Kagaku Koza (New Lecture Course of Experimental Chemistry), Vol. 14, p. 93 (Maruzen); a reaction of an α,β-unsaturated ester with a sulphur ylide described in Advance Organic Chemistry, 3d Edition, p. 773 (Wiley-Interscience).

Furthermore, the compounds of formula (VIII) can also be obtained by, decarboxylation of the corresponding cyclopropane: dicarboxylic acids as described in Beilstein, EII9, p. 3.

The compounds of formula (VI) used as starting material in the above method e) can be produced, for example, by the following method described in Berichte, Vol. 28, pp.74–76 (1895), that is, reaction of a compound represented by the formula

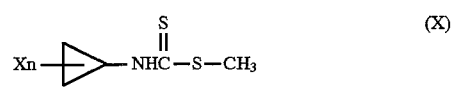

wherein

X and n are as defined above, with sodium azide.

Dithiocarbamic acid esters of above formula (X) can easily be obtained, for example, by the reaction of methanenthiol with a compound represented by the formula

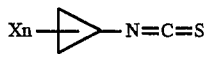 (XI)

wherein

X and n are as defined above, or reaction of a compound represented by the formula

 (XII)

wherein

X and n are as defined above, with carbon disulphide followed by further reaction with a methylating agent, e.g., dimethyl sulphate or iodomethane.

The compounds of above formula (XI) can be obtained for example, by the method, described in J. Hererocycl. Chem., (1990), Vol. 27 (5), pp. 1191–1195.

Also, the compounds of formula (XII) can be obtained by the Hoffman reaction of a corresponding cyclopropane carboxylic acid amide described in Organic Reactions, Vol. 3, p. 287 or the decomposing reaction of a corresponding cyclopropane carbonyl azide, e.g., Curtius rearrangement, described in the same article p. 337.

The compounds of formula (VII) used in the production method e) as the starting materials are known per se and are specifically exemplified by ethyleneoxide or 1,2-epoxypropane.

Typical examples of compounds of above formula (II) are:

1-cyclopropyl-5(4H)-tetrazolinone,
1-(2-methylcyclopropyl)-5(4H)-tetrazolinone,
1-(1-methylcyclopropyl)-5(4H)-tetrazolinone,
1-(2,2-dimethylcyclopropyl)-5(4H)-tetrazolinone,
1-(2,3-dimethylcyclopropyl)-5(4H)-tetrazolinone,
1-(1,2,2-trimethylcyclopropyl)-5(4H)-tetrazolinone,
1-(1,2,3-trimethylcyclopropyl)-5(4H)-tetrazolinone,
1-(2,2,3,3-tetramethylcyclopropyl)-5(4H)-tetrazolinone,
1-(1- ethylcyclopropyl)-5(4H)-tetrazolinone,
1-(2-ethylcyclopropyl)-5(4H)-tetrazolinone,
1-(1-ethyl-2-methylcyclopropyl)-5(4H)-tetrazolinone,
1-(2-ethyl-3-methylcyclopropyl)-5(4H)-tetrazolinone,
1-(2-n-propylcyclopropyl)-5(4H)-tetrazolinone,
1-(2-isopropylcyclopropyl)-5(4H)-tetrazolinone,
1-(2,2-dimethyl-3-vinylcyclopropyl)-5(4H)-tetrazolinone,
1-[2,2-dimethyl-3-(2-methyl-1-propenyl) cyclopropyl]-5(4H)-tetrazolinone,
1-(2,2-dichlorocyclopropyl)-5(4H)-tetrazolinone,
1-(2,2-dibromocyclopropyl)-5(4H)-tetrazolinone,
1-(2,2-difluorocyclopropyl)-5(4H)-tetrazolinone,
1-(2-chloro-2-fluorocyclopropyl)-5(4H)-tetrazolinone,
1-(2-chloro-2-fluoro-1-methylcyclopropyl)-5(4H)-tetrazolinone,
1-(2,2-dibromo-1-methylcyclopropyl)-5(4H)-tetrazolinone,
1-(2,2-dibromo-1,3-dimethylcyclopropyl)-5(4H)-tetrazolinone,
1-(2,2-dichloro-1-methylcyclopropyl)-5(4H)-tetrazolinone
1-(2,2-dichloro-1,3-dimethylcyclopropyl)-5(4H)-tetrazolinone,
1-(2,2-difluoro-1-methylcyclopropyl)-5(4H)-tetrazolinone,
1-(2,2-dichloro-3-methylcyclopropyl)-5(4H)-tetrazolinone,
1-(2,2-dichloro-1,3,3-trimethylcyclopropyl)-5(4H)-tetrazolinone,
1-(2,2-dichloro-1-ethylcyclopropyl)-5(4H)-tetrazolinone,
1-(2,2-dichloro-1-ethyl-3-methylcyclopropyl)-5(4H)-tetrazolinone,
1-(2,2-dichloro-1-isopropylcyclopropyl)-5(4H)-tetrazolinone, etc.

Compounds of formula (III) which are reared with the compounds of above formula (II) include carbamoyl chlorides which are well known, such as:

N,N-diethylcarbamoyl chloride,
N-cyclohexyl-N-ethylcarbamoyl chloride,
N,N-di-n-propylcarbamoyl chloride,
N-cyclopropyl-N-n-propylcarbamoyl chloride,
N-cyclopentyl-N-n-propylcarbamoyl chloride,
N-diallylcarbamoyl chloride,
N-dipropargylcarbamoyl chloride,
N-isopropyl-N-phenylcarbamoyl chloride,
N-(2-chlorophenyl)-N-isopropylcarbamoyl chloride,
N-(3-chlorophenyl)-N-isopropylcarbamoyl chloride,
N-(4-chlorophenyl)-N-isopropylcarbamoyl chloride,
N-isopropyl-N-p-tolylcarbamoyl chloride,
N-benzyl-N-isopropylcarbamoyl chloride,
N-(2,3-epoxypropan-1-yl)-N-phenylcarbamoyl chloride,
N-(2-acetylphenyl)-N-isopropylcarbamoyl chloride,
N-isopropyl-N-2-(1-methoxyiminoethyl) phenylcarbamoyl chloride,
1-indolinylcarbonyl chloride,
1,2,3,4-tetrahydroquinolin-1-ylcarbonyl chloride,
2-methyl-1,2,3,4-tetrahydroquinolin-1-ylcarbonyl chloride,
N-(1,1-dimethylpropargyl)-N-phenylcarbamoyl chloride,
N-allyl-N-phenylcarbamoyl chloride,
N-methyl-N-phenylcarbamoyl chloride,
N-ethyl-N-phenylcarbamoyl chloride,
N-n-propyl-N-phenylcarbamoyl chloride,
N-cyclohexyl-N-isopropylcarbamoyl chloride,
N-isopropyl-N-(4-nitrophenyl)carbamoyl chloride,
N-isopropyl-N-(4-cyanophenyl)carbamoyl chloride, etc.

Method is usually carried out in an organic solvent which is inert to the reaction. Inert organic solvents useful in such a reaction include aliphatic, alicyclic and aromatic hydrocarbons (which may optionally be chlorinated) as exemplified by pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers as exemplified by diethyl ether, methyl ethyl ether, diisopropyl ether, dibutyl ether, dioxane, dimethoxyethane (DME), tetrahydrofuran (THF) and diethyleneglycol dimethyl ether (DGM); and acid amides as exemplified by dimethyl formamide (DMF), dimethyl acetoamide (DMA), N-methyl pyrrolidone, 1,3-dimethyl-2-imidazolidinone and hexamethyl phosphoric triamide (HMPA).

The process can be carried out in the presence of a base such as 4-dimethylamino pyridine (DMAP). DMAP as the base, the process can usually be carried out at a temperature of about −10° to about 200° C., preferably at about 25° to about 140° C. under atmospheric pressure but it is possible to conduct the reaction under elevated or reduced pressure.

Furthermore, the process can also be conducted using a base other than DMAP e.g. inorganic bases (such as sodium carbonate, potassium carbonate, sodium hydroxide, potassium hydroxide, etc.), alkali alcoholates (such as sodium methoxide, sodium ethoxide, potassium tert-butoxide, etc.), sodium hydride, potassium hydride, lithium hydride, organic bases such as triethylamine, 1,1,4,4-tetramethyl ethylenediamine, N,N-dimethylaniline, pyridine, etc.) and others.

In carrying out such a reaction using any of these bases, the compounds of formula (I) can be obtained selectively by using DMAP as the catalyst.

The reaction temperature in such event is usually within the range of about 0° to about 150° C., preferably about 25° to about 100° C., and it is preferable to carry out the reaction under atmospheric pressure but optionally it can also be carried out under elevated or reduced pressure.

Thus, the compounds of formula (I) according to the invention can be produced by reacting about 1 mole to about 1.5 moles of a compound of formula (III) with 1 mole of a compound of formula (II) in the presence of about 1 mole to about 1.5 moles of DMAP as the catalyst in an inert solvent as referred to above. Alternatively, the compounds of formula (I) can be produced by, the reaction of about 1 mole to about 1.5 moles of a compound of formula (III) with 1 mole of a compound of formula (II) in the presence of about 0.01 mole to about 0.3 mole of DMAP as the catalyst and about 1 mole to about 1.5 moles of, fur example, potassium carbonate as the base in an inert solvent as referred to above.

The compounds of formula (I) according to the invention can be isolated and purified by any means such as crystallization, chromatography, and the like.

Method b) can be conducted using boron trifluoride ethyl etherate as the catalyst. The reaction temperature may usually be about 0° to about 200° C., preferably about 50° to about 150° C. and the reaction should preferably be conducted under atmospheric pressure but it is also possible to conduct it under elevated or reduced pressure.

Method b) can usually be carried out by reacting about 1 mole to about 2 moles of trimethyl silyl azide with 1 mole of the compound of formula (IV) in the presence of about 0.005 mole to about 0.01 mole of boron trifluoride ethyl etherate as the catalyst.

Method c) is usually conducted in a polar solvent such as an acid amide, e.g. dimethyl formamide, dimethyl acetoamide and the like and sulphoxides such as dimethyl sulphoxide, sulpholane,and the like. The reaction temperature may be set at about 0° to about 200° C. in general, about 20° to about 150° C. preferably and the reaction should preferably be conducted under atmospheric pressure but it may also be conducted under elevated or reduced pressure.

Method c) can usually be conducted by reacting about 1 mole to about 1.5 moles of sodium azide with 1 mole of the compound of formula IV) in the presence of about 0.05 mole to about 1 mole of aluminum chloride as the catalyst in a polar solvent such as dimethyl formamide.

Method d) can be carried out at temperatures of, for instant, about 0 to about 200° C., preferably about 25° to about 130° C., under atmospheric pressure but it is also possible to carry it out under elevated pressure or reduced pressure.

Method d) can usually be carried out by reacting about 2 moles to about 4 moles of trimethyl silyl azide with 1 mole of the compound of formula (V).

Method e) is usually conducted in a solvent which is inert to the reaction, e.g. water and alcohols (such as methanol, ethanol, isopropanol, and the like).

Method e) can be carried out in the presence of, for instance, an inorganic base (such as sodium hydrogen carbonate, potassium hydrogen carbonate, sodium carbonate, potassium carbonate, sodium hydroxide, potassium hydroxide, and the like).

The reaction temperature in method e) can be set usually at about −30° to 50° C., preferably at about 0° to about 30° C. and the reaction is preferably conducted under atmospheric pressure but it is possible to conduct it under elevated pressure or reduced pressure.

Method e) can usually be carried out by reacting about 1 mole to about 1.3 moles of the compound of formula (VII) with 1 mole of the compound of formula (VI) in the presence of a base in an inert solvent.

The active compounds of formula (I) according to the invention have, as shown in the test examples hereinbelow excellent herbicidal activity so that they can be used as herbicides for controlling weeds. The term "weeds" in a broad sense means all plants which grow in undesired loci.

The compounds of the invention act either as non-selective or selective herbicides depending on the concentration employed. The active compounds of the invention can be used as selective herbicides between, for example, the weeds and cultivated plants shown below.

Dicotyledon weeds of the genera: Sinapis, Lepidium, Galium, Stellaria, Chenopodium, Urtica, Senecio, Amaranthus, Portulaca, Xanthium, Ipomoea, Polygonum, Ambrosia, Cirsium, Sonchus, Solanum, Rorippa, Lamium, Veronica, Datura, Viola, Galeopsis, Papaver, Centaurea, Galinsoga, Rotala, Lindernia, etc.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita, etc.

Monocotyledon weeds of the genera: Echinochloa, Setaria, Panicum, Digitaria, Phleum, Poa, Festuca, Eleusine, Lolium, Bromus, Avena, Cyperus, Sorghum, Agropyron, Monochoria, Fimbristylis, Sagittaria, Eleocharis, Scirpus, Paspalum, Ischaemum, Agrostis, Alopecurus, Cynodon, etc.

Monocotyledon cultures of the genera: Oryza, zea, Triticum, Hordeum, Avena, Secale, Sorghum, Panicum, Saccharum, Ananas, Asparagus, Allium, etc.

However, the use of the active compounds of formula (I) according to the invention is in no way restricted to the above genera, but also extends in the same manner to other plants. Further, the active compounds of the invention are suitable, depending on concentration, for the total combating of weeds, for example on industrial terrain, rail tracks, and on paths and squares with or without tree plantings.

Equally, the active compounds of the invention can be employed for combating weeds in perennial cultures, for example afforestations, decorative tree plantations, orchards, vineyards, citrus groves, nuts orchards, banana plantations, coffee plantations, tea plantations, rubber plantations, oil palm plantations, cocoa plantations, soft fruit plantations and hopfields, and for the selective combating of weeds in annual cultures.

The active compounds of the invention can be converted to the customary formulations, such as solutions, emulsions, wettable powders, suspensions, powders, soluble powders, dusting agents, granules, tablets, suspension-emulsion concentrates, very fine capsules in polymeric substances, natural and synthetic materials impregnated with active compound, etc.

Those formulations are produced in manner known per se, for example, by mixing the active compounds with extenders, that is liquid solvents and/or solid carriers, optionally with the use of surface-active agents, that is emulsifying agents and/or dispersing agents and/or foam-forming agents.

In case of the use of water as an extender, organic solvents can be used as auxiliary solvents. As liquid solvents, there are suitable in the main: aromatic hydrocarbons, such as xylene, toluene or alkyl naphthalenes; chlorinated aromatic hydrocarbons and chlorinated aliphatic hydrocarbons; such as chlorobenzenes, chloroethylenes or methylene chloride; aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone; strongly polar solvents, such as dimethylformamide and dimethylsulphoxide.

As solid carriers there are suitable: for example, ammonium salts and ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn and tobacco stalks.

As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products.

As dispersing agents there are suitable: for example lignin-sulphite waste liquors and methylcellulose.

Adhesives may also be used optionally in formulations such as powders, granules, natural and synthetic materials impregnated with active compound or emulsions, and the followings are examples of such adhesives:

carboxymethylcellulose and natural and synthetic polymers such as gum arabic, polyvinyl alcohol and polyvinyl acetate, as well as natural phospholipids, such as cephalins and lecithins, and synthetic phospholipids. As further additives there are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of metals, for example iron, manganese, boron, copper, molybdenum and zinc.

The formulations in general contain between 0.1 and 95% by weight preferably between 0.5 and 90% by weight, of the active compound.

The active compounds of formula (I) according to the invention can be used for controlling of weeds as they are or in the form of such formulations and can be mixed with any known herbicides. The mixture may be either prepared in advance in the form of a final formulation or prepared by tank-mixing immediately before use.

It is possible to mix the active compounds of formula (I) according to the invention with a chemical injury-mitigating agent and the applicability as a selective herbicide can be more broadened by this mixing.

A chemical injury-mitigating agent is exemplified by 1-(α,α-dimethyl benzyl)-3-p-tolyl urea.

The active compounds of formula (I) according to the invention may be applied by any conventional method such as watering, atomizing, powder spreading or granule scattering.

The active compounds of formula (I) according to the invention may be applied at any stage of preemergence or postemergence. Also, they can be incorporated into the soil before sowing.

The amount of active compound applied may be varied within a wide range depending on the nature of desired effect, the target plants(s) the location of application, the time of application, and the like but, as a tentative measure, the amount exemplified by about 0.001 kg/ha to about 10 kg/ha preferably about 0.01 kg/ha–about 5 kg/ha.

The following examples illustrate the production and uses of the compounds of the invention, but they should not be regarded as limiting the invention in any way. The term "part(s)" therein means "part(s) by weight" unless otherwise noted.

EXAMPLES

Synthesis Example 1

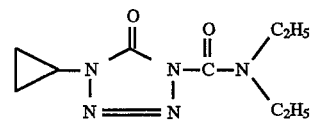

1-Cyclopropyl-5(4H)-tetrazolinone (1 g), 4-dimethylaminopyridine (1.1 g) and diethylcarbamoyl chloride (1.2 g) are suspended in toluene (50 ml) and stirred for 5 to 6 hours at 50° to 55° C. After cooling by standing, the organic layer is washed successively with water 1% hydrochloric acid, water, saturated aqueous solution of sodium hydrogen carbonate and water. After drying of the organic layer over anhydrous sodium sulphate, the solvent is distilled off under reduced pressure and the residue is purified by column chromatography (eluent: chloroform) to give 1-cyclopropyl-4-diethylcarbamoyl-5(4H)-tetrazolinone (1.8 g) $n_D^{20}$ 1.5005

The compound obtained in the foregoing Synthesis Example 1, alone with additional compounds of formula (I) according to the invention, obtainable by the above-mentioned procedure, are shown in the following Table 1.

TABLE 1

$$\text{Xn}-\triangleleft-\underset{\underset{N=N}{|}}{N}-\overset{O}{\overset{\|}{C}}-\underset{\underset{N=N}{|}}{N}-\overset{O}{\overset{\|}{C}}-N\underset{R^2}{\overset{R^1}{<}} \quad (I)$$

| Compound No. | $X_a$ | $R^1$ | $R^2$ | physical property |
|---|---|---|---|---|
| 1 | — | $C_2H_5$ | $C_2H_5$ | $n_D^{20}$ 1.5005 |
| 2 | — | " | cyclohexyl (H) | $n_D^{20}$ 1.5112 |
| 3 | — | $C_3H_7$-n | $C_3H_7$-n | |
| 4 | — | " | cyclopropyl | |
| 5 | — | " | cyclopentyl (H) | |
| 6 | — | $-CH_2CH=CH_2$ | $-CH_2CH=CH_2$ | |
| 7 | — | $-CH_2C\equiv CH$ | $-CH_2C\equiv CH$ | |
| 8 | — | $C_3H_7$-i | phenyl | $n_D^{20}$ 1.5324 |
| 9 | — | " | 2-F-phenyl | |
| 10 | — | " | 3-F-phenyl | |
| 11 | — | " | 4-F-phenyl | $n_D^{20}$ 1.5252 |
| 12 | — | " | 2-Cl-phenyl | $n_D^{20}$ 1.5530 |
| 13 | — | " | 3-Cl-phenyl | mp. 82.5~83.5° C. |
| 14 | — | " | 4-Cl-phenyl | mp. 94–97° C. |

TABLE 1-continued

Structure (I): Xn-cyclopropyl-N-C(=O)-N(tetrazole)-N=N, with C(=O)-N(R¹)(R²)

| Compound No. | Xₐ | R¹ | R² | physical property |
|---|---|---|---|---|
| 15 | — | C₃H₇-i | 2,3-diCl-phenyl | |
| 16 | — | " | 2,4-diCl-phenyl | |
| 17 | — | " | 3,5-diCl-phenyl | |
| 18 | — | " | 3-Cl-4-CH₃-phenyl | |
| 19 | — | " | 2-Br-phenyl | |
| 20 | — | " | 3-Br-phenyl | |
| 21 | — | " | 4-Br-phenyl | |
| 22 | — | " | 2-CF₃-phenyl | |
| 23 | — | " | 3-CF₃-phenyl | |
| 24 | — | " | 4-CF₃-phenyl | |

TABLE 1-continued (I) structure: Xn-cyclopropyl-N(-C(=O)-)N=N-N(-C(=O)-N(R¹)(R²))

| Compound No. | X_n | R¹ | R² | physical property |
|---|---|---|---|---|
| 25 | — | " | 2-OCH₃-phenyl | |
| 26 | — | " | 2-OCF₃-phenyl | |
| 27 | — | " | 2-OCHF₂-phenyl | |
| 28 | — | C₃H₇-i | 2-SCF₃-phenyl | |
| 29 | — | " | 2-CH₃-phenyl | |
| 30 | — | " | 3-CH₃-phenyl | |
| 31 | — | " | 4-CH₃-phenyl | mp. 84–86° C. |
| 32 | — | " | 2,4-(CH₃)₂-phenyl | |
| 33 | — | " | 2-C₂H₅-phenyl | |
| 34 | — | " | 4-NO₂-phenyl | |

TABLE 1-continued
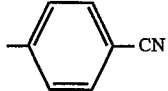
| Compound No. | $X_a$ | $R^1$ | $R^2$ | physical property |
|---|---|---|---|---|
| 35 | — | " | 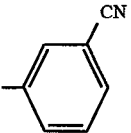 | |
| 36 | — | " | 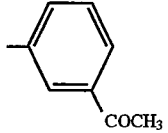 | |
| 37 | — | " | 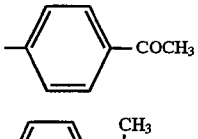 | $n_D^{20}$ 1.5413 |
| 38 | — | " | 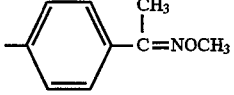 | |
| 39 | — | " | 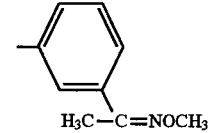 | |
| 40 | — | " | 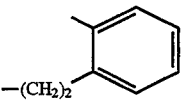 | $n_D^{20}$ 1.5300 |
| 41 | — | —(CH$_2$)$_4$— | | |
| 42 | — | —(CH$_2$)$_3$—CH(CH$_3$)— | | |
| 43 | — | —(CH$_2$)$_2$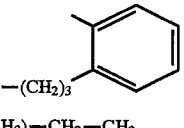 | | |
| 44 | — | —(CH$_2$)$_3$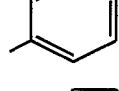 | | $n_D^{20}$ 1.5678 |
| 45 | — | —CH(CH$_3$)—CH$_2$—CH$_2$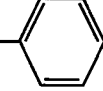 | | mp. 103–106° C. |
| 46 | — | —C(CH$_3$)$_2$—C≡CH |  | $n_D^{20}$ 1.5440 |
| 47 | — | —CH(CH$_3$)—C≡CH | " | $n_D^{20}$ 1.5430 |
| 48 | — | —CH$_2$C≡CH | " | |
| 49 | — | —$_2$CH=CH$_2$ | " | $n_D^{20}$ 1.5555 |

TABLE 1-continued $$\text{Xn}-\triangle-\underset{\underset{N}{|}}{N}-\underset{\underset{||}{O}}{C}-\underset{\underset{N}{|}}{N}-\underset{\underset{||}{O}}{C}-N\genfrac{}{}{0pt}{}{R^1}{R^2} \quad (I)$$

| Compound No. | $X_a$ | $R^1$ | $R^2$ | physical property |
|---|---|---|---|---|
| 50 | — | $C_3H_7$-i | —CH$_2$—(phenyl) | $n_D^{20}$ 1.5317 |
| 51 | — | $C_3H_7$-n | (phenyl) | $n_D^{20}$ 1.5407 |
| 52 | — | CH$_3$ | " | $n_D^{20}$ 1.5532 |
| 53 | — | C$_2$H$_5$ | " | $n_D^{20}$ 1.5480 |
| 54 | — | C$_4$H$_9$-n | " | |
| 55 | — | C$_4$H$_9$-sec | " | $n_D^{20}$ 1.5345 |
| 56 | — | C$_4$H$_9$-iso | " | |
| 57 | — | (phenyl) | " | |
| 58 | — | —C(CH$_3$)$_2$C≡CH | (2-Cl-phenyl) | |
| 59 | — | " | (3-Cl-phenyl) | |
| 60 | — | " | (4-Cl-phenyl) | |
| 61 | — | —C(CH$_3$)$_2$C≡CH | (2-Br-phenyl) | |
| 62 | — | " | (3-Br-phenyl) | |
| 63 | — | " | (4-Br-phenyl) | $n_D^{20}$ 1.5510 |
| 64 | — | " | (4-CH$_3$-phenyl) | |

TABLE 1-continued

Structure (I):
Xn-cyclopropyl-N(—N=N—)N-C(=O)-N-C(=O)-NR¹R²

| Compound No. | X$_a$ | R¹ | R² | physical property |
|---|---|---|---|---|
| 65 | — | " | 4-CF$_3$-C$_6$H$_4$- | |
| 66 | — | " | 4-CN-C$_6$H$_4$- | |
| 67 | — | " | 4-NO$_2$-C$_6$H$_4$- | |
| 68 | — | —CH(CH$_3$)C≡CH | 4-Cl-C$_6$H$_4$- | |
| 69 | — | " | 2-Cl-C$_6$H$_4$- | |
| 70 | — | " | 3-Cl-C$_6$H$_4$- | |
| 71 | — | " | 4-CH$_3$-C$_6$H$_4$- | |
| 72 | — | " | 4-Br-C$_6$H$_4$- | |
| 73 | — | C$_6$H$_5$- | —CH$_2$-(oxiranyl) | n$_D^{20}$ 1.5499 |
| 74 | — | —C(CH$_3$)$_2$C≡CH | 2,4-Cl$_2$-C$_6$H$_3$- | |
| 75 | — | —CH(CH$_3$)C≡CH | 3,5-Cl$_2$-C$_6$H$_3$- | |

TABLE 1-continued
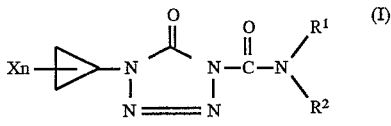
| Compound No. | $X_a$ | $R^1$ | $R^2$ | physical property |
|---|---|---|---|---|
| 76 | — | —C(CH$_3$)$_2$C≡CH | 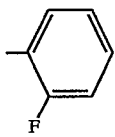 | |
| 77 | — | " | 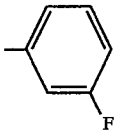 | |
| 78 | — | " |  | |
| 79 | — | —CH(CH$_3$)C≡CH | " | |
| 80 | — | " | 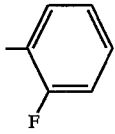 | |
| 81 | — | C$_3$H$_7$-i | 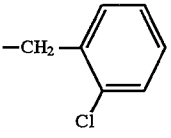 | |
| 82 | — | " | 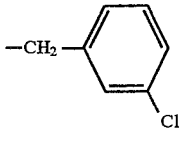 | |
| 83 | — | " | 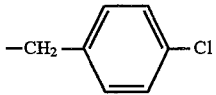 | |
| 84 | — | " | 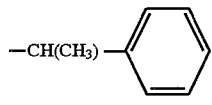 | |
| 85 | — | " | 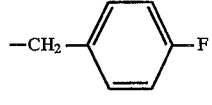 | |
| 86 | — | " | 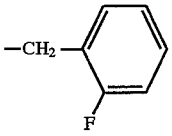 | |

TABLE 1-continued $$Xn-\triangle-N-\underset{\underset{N}{\parallel}}{\overset{\overset{O}{\parallel}}{C}}-N-\underset{\underset{N}{\parallel}}{\overset{\overset{O}{\parallel}}{C}}-N\underset{R^2}{\overset{R^1}{<}} \quad (I)$$

| Compound No. | $X_a$ | $R^1$ | $R^2$ | physical property |
|---|---|---|---|---|
| 87 | — | " | $-CH_2-\phi-CH_3$ | |
| 88 | — | " | $-CH_2-\phi-Br$ | |
| 89 | — | " | $-CH_2-\phi-NO_2$ | |
| 90 | — | " | $-CH_2-\phi(Cl)(Cl)$ (2,4-diCl) | |
| 91 | — | $C_3H_7\text{-}i$ | $-CH_2-\phi-CF_3$ (3-) | |
| 92 | — | $-C(CH_3)_2C\equiv CH$ | $-CH_2-\phi$ | |
| 93 | — | $-CH(CH_3)C\equiv CH$ | " | " |
| 94 | — | $-C(CH_3)_2C\equiv CH$ | $-CH_2-\phi-Cl$ | |
| 95 | — | $C_3H_7\text{-}i$ | cyclohexyl | mp. 87–90.5° C. |
| 96 | 1-$CH_3$ | $C_2H_5$ | $C_2H_5$ | |
| 97 | " | " | cyclohexyl | |
| 98 | " | $C_3H_7\text{-}n$ | $C_3H_7\text{-}n$ | |
| 99 | " | " | cyclopropyl | |
| 100 | " | " | cyclopentyl | |
| 101 | " | $-CH_2CH=CH_2$ | $-CH_2CH=CH_2$ | |

TABLE 1-continued
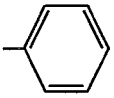
| Compound No. | $X_a$ | $R^1$ | $R^2$ | physical property |
|---|---|---|---|---|
| 102 | " | $C_3H_7$-i | phenyl | $n_D^{20}$ 1.5148 |
| 103 | " | " | 2-F-phenyl | |
| 104 | " | " | 4-F-phenyl | mp. 71–72.5 |
| 105 | " | " | 2-Cl-phenyl | |
| 106 | " | " | 3-Cl-phenyl | |
| 107 | 1-$CH_3$ | $C_3H_7$-i | 4-Cl-phenyl | mp. 90–93° C. |
| 108 | " | " | 2,4-diCl-phenyl | |
| 109 | " | " | 3-Cl-4-$CH_3$-phenyl | |
| 110 | " | " | 4-Br-phenyl | |
| 111 | " | " | 3-$CF_3$-phenyl | |
| 112 | " | " | 4-$OCF_3$-phenyl | |

TABLE 1-continued
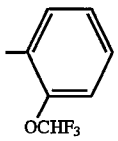
| Compound No. | $X_a$ | $R^1$ | $R^2$ | physical property |
|---|---|---|---|---|
| 113 | " | " | 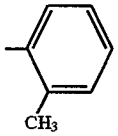 | |
| 114 | " | " | 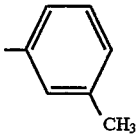 | |
| 115 | " | " | 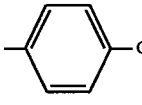 | |
| 116 | " | " | 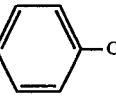 | |
| 117 | " | " | 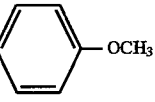 | |
| 118 | " | " | 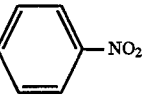 | |
| 119 | " | " | 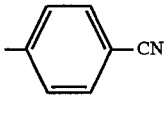 | |
| 120 | " | " | —⟨C₆H₄⟩—CN | |
| 121 | " | —(CH₂)₄— | | |
| 122 | 1-CH₃ | —(CH₂)₃—CH(CH₃)— | | |
| 123 | " | —(CH₂)₂—⟨o-tolyl⟩ | | |
| 124 | " | —(CH₂)₃—⟨o-tolyl⟩ | | |
| 125 | " | —CH(CH₃)—CH₂CH₂—⟨o-tolyl⟩ | | mp. 100~101° C. |

TABLE 1-continued $$Xn-\triangle-\underset{\underset{N=N}{|}}{N}-\overset{O}{\overset{\|}{C}}-\underset{\underset{N=N}{|}}{N}-\overset{O}{\overset{\|}{C}}-N\underset{R^2}{\overset{R^1}{<}} \quad (I)$$

| Compound No. | $X_a$ | $R^1$ | $R^2$ | physical property |
|---|---|---|---|---|
| 126 | " | —C(CH$_3$)$_2$C≡CH | 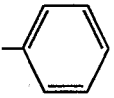 | |
| 127 | " | —CH(CH$_3$)C≡CH | " | |
| 128 | " | —CH$_2$C≡CH | " | |
| 129 | " | —CH$_2$CH=CH$_2$ | " | |
| 130 | " | C$_3$H$_7$-i | 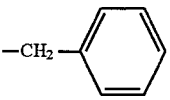 | |
| 131 | " | C$_3$H$_7$-n | 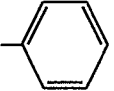 | |
| 132 | " | CH$_3$ | " | |
| 133 | " | C$_2$H$_5$ | " | |
| 134 | " | C$_4$H$_9$-n | " | |
| 135 | " | C$_4$H$_9$-sec | " | |
| 136 | " | C$_4$H$_9$-i | " | |
| 137 | " | —C(CH$_3$)$_2$C≡CH | 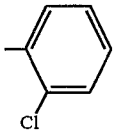 | |
| 138 | 1-CH$_3$ | —C(CH$_3$)$_2$C≡CH | 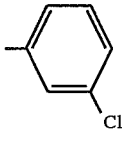 | |
| 139 | " | " | 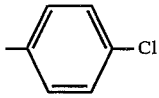 | |
| 140 | " | " | 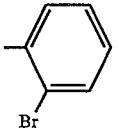 | |
| 141 | " | " | 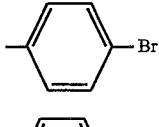 | |
| 142 | " | " |  | |

TABLE 1-continued

Structure (I): Xn-cyclopropyl-N-N(=O)-N-(tetrazole)-N-C(=O)-N(R¹)(R²)

| Compound No. | $X_a$ | $R^1$ | $R^2$ | physical property |
|---|---|---|---|---|
| 143 | " | " | 4-CF₃-C₆H₄- | |
| 144 | " | " | 4-CN-C₆H₄- | |
| 145 | " | " | 4-NO₂-C₆H₄- | |
| 146 | " | —CH(CH₃)C≡CH | 2-Cl-C₆H₄- | |
| 147 | " | " | 3-Cl-C₆H₄- | |
| 148 | " | " | 4-Cl-C₆H₄- | |
| 149 | " | " | 4-Br-C₆H₄- | |
| 150 | " | " | 4-F-C₆H₄- | |
| 151 | " | " | 4-CH₃-C₆H₄- | |
| 152 | " | C₆H₅- | —CH₂-(epoxide) | |
| 153 | " | —C(CH₃)₂C≡CH | 3-F,4-Cl-C₆H₃- | |

TABLE 1-continued structure (I): Xn-cyclopropyl-N(-C(=O)-)N-N=N-N(-C(=O)-)-N(R¹)(R²)

| Compound No. | $X_a$ | $R^1$ | $R^2$ | physical property |
|---|---|---|---|---|
| 154 | 1-CH$_3$ | —C(CH$_3$)$_2$C≡CH | 2-F-phenyl | |
| 155 | " | " | 3-F-phenyl | |
| 156 | " | " | 4-F-phenyl | |
| 157 | " | —CH(CH$_3$)C≡CH | 4-F-phenyl | |
| 158 | " | " | 2-F-phenyl | |
| 159 | " | " | 3-F-phenyl | |
| 160 | " | C$_3$H$_7$-i | —CH$_2$-(2-Cl-phenyl) | |
| 161 | " | " | —CH$_2$-(4-Cl-phenyl) | |
| 162 | " | " | —CH(CH$_3$)-(4-Cl-phenyl) | |
| 163 | " | " | —CH$_2$-(4-F-phenyl) | |
| 164 | " | " | —CH$_2$-(2-F-phenyl) | |

TABLE 1-continued $$\text{Xn}-\triangle-\underset{\underset{N}{|}}{N}-\underset{\underset{\|}{O}}{C}-\underset{\underset{N}{|}}{N}-\underset{\underset{\|}{O}}{C}-N\genfrac{}{}{0pt}{}{R^1}{R^2} \quad (I)$$

| Compound No. | $X_a$ | $R^1$ | $R^2$ | physical property |
|---|---|---|---|---|
| 165 | " | " | −CH$_2$−(2-CH$_3$-C$_6$H$_4$) | |
| 166 | " | " | −CH$_2$−(4-Br-C$_6$H$_4$) | |
| 167 | " | −C(CH$_3$)$_2$C≡CH | −CH$_2$−C$_6$H$_5$ | |
| 168 | " | C$_3$H$_7$-i | 3-(COCH$_3$)-C$_6$H$_4$− | |
| 169 | 1-CH$_3$ | C$_3$H$_7$-i | 3-(H$_3$C−C=NOCH$_3$)-C$_6$H$_4$− | |
| 170 | " | " | cyclohexyl | |
| 171 | 2-CH$_3$ | C$_2$H$_5$ | C$_2$H$_5$ | |
| 172 | " | " | cyclohexyl | |
| 173 | " | C$_3$H$_7$-n | C$_3$H$_7$-n | |
| 174 | " | " | cyclopropyl | |
| 175 | " | " | cyclopentyl | |
| 176 | " | −CH$_2$CH=CH$_2$ | −CH$_2$CH=CH$_2$ | |
| 177 | " | C$_3$H$_7$-i | C$_6$H$_5$− | $n_D^{20}$ 1.5276 |
| 178 | " | " | 2-F-C$_6$H$_4$− | |

TABLE 1-continued $$\text{Xn} - \triangle - \underset{\underset{N=\!=\!N}{N}}{N} - \overset{O}{\underset{\|}{C}} - N - \overset{O}{\underset{\|}{C}} - N \underset{R^2}{\overset{R^1}{<}} \quad (I)$$

| Compound No. | $X_a$ | $R^1$ | $R^2$ | physical property |
|---|---|---|---|---|
| 179 | " | " | 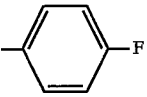 4-F-C$_6$H$_4$ | $n_D^{20}$ 1.5171 |
| 180 | " | " | 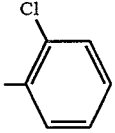 2-Cl-C$_6$H$_4$ | |
| 181 | " | " | 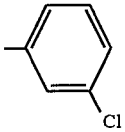 3-Cl-C$_6$H$_4$ | |
| 182 | " | " | 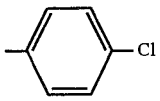 4-Cl-C$_6$H$_4$ | $n_D^{20}$ 1.5311 |
| 183 | " | " | 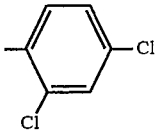 2,4-Cl$_2$-C$_6$H$_3$ | |
| 184 | " | " | 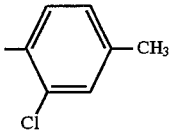 3-Cl-4-CH$_3$-C$_6$H$_3$ | |
| 185 | 2-CH$_3$ | C$_3$H$_7$-i | 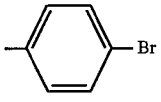 4-Br-C$_6$H$_4$ | |
| 186 | " | " | 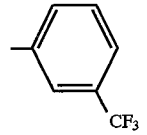 3-CF$_3$-C$_6$H$_4$ | |
| 187 | " | " | 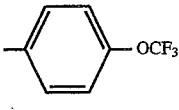 4-OCF$_3$-C$_6$H$_4$ | |
| 188 | " | " | 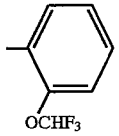 2-OCHF$_2$-C$_6$H$_4$ | |
| 189 | " | " | 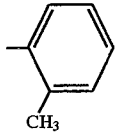 3-CH$_3$-C$_6$H$_4$ | |

TABLE 1-continued

Structure (I): Xn-cyclopropyl-N-N=N-N(linked to C(=O)-C(=O)-N(R¹)(R²))

| Compound No. | $X_a$ | $R^1$ | $R^2$ | physical property |
|---|---|---|---|---|
| 190 | " | " | 3-CH₃-C₆H₄- | |
| 191 | " | " | 4-CH₃-C₆H₄- | $n_D^{20}$ 1.5207 |
| 192 | " | " | 4-C₂H₅-C₆H₄- | |
| 193 | " | " | 4-OCH₃-C₆H₄- | |
| 194 | " | " | 4-NO₂-C₆H₄- | |
| 195 | " | " | 4-CN-C₆H₄- | |
| 196 | " | —(CH₂)₄— | | |
| 197 | " | —(CH₂)₃—CH(CH₃)— | | |
| 198 | " | —(CH₂)₂- (2-CH₃-C₆H₄) | | |
| 199 | " | —(CH₂)₃- (2-CH₃-C₆H₄) | | |
| 200 | " | —CH(CH₃)—CH₂CH₂- (2-CH₃-C₆H₄) | | $n_D^{20}$ 1.5444 |
| 201 | 2-CH₃ | —C(CH₃)₂C≡CH | C₆H₅- | $n_D^{20}$ 1.5289 |
| 202 | " | —CH(CH₃)C≡CH | " | $n_D^{20}$ 1.5353 |
| 203 | " | —CH₂C≡CH | " | |
| 204 | " | —CH₂CH=CH₂ | " | |

TABLE 1-continued
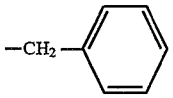
| Compound No. | $X_a$ | $R^1$ | $R^2$ | physical property |
|---|---|---|---|---|
| 205 | " | $C_3H_7$-i | —CH₂—C₆H₅ | $n_D^{20}$ 1.5245 |
| 206 | " | $C_3H_7$-n | —C₆H₅ | |
| 207 | " | $CH_3$ | " | |
| 208 | " | $C_2H_5$ | " | |
| 209 | " | $C_4H_9$-n | " | |
| 210 | " | $C_4H_9$-sec | " | |
| 211 | " | $C_4H_9$-i | —C₆H₅ | |
| 212 | " | —C(CH₃)₂C≡CH | 2-Cl-C₆H₄ | |
| 213 | " | " | 3-Cl-C₆H₄ | |
| 214 | " | " | 4-Cl-C₆H₄ | |
| 215 | " | " | 2-Br-C₆H₄ | |
| 216 | " | " | 3-Br-C₆H₄ | |
| 217 | " | " | 4-Br-C₆H₄ | |
| 218 | 2-$CH_3$ | —C(CH₃)₂C≡CH | 4-CH₃-C₆H₄ | |

TABLE 1-continued $$Xn\text{-}\triangle\text{-}N\text{-}C(=O)\text{-}N\text{-}C(=O)\text{-}NR^1R^2 \quad (I)$$
(with N=N in ring)

| Compound No. | $X_a$ | $R^1$ | $R^2$ | physical property |
|---|---|---|---|---|
| 219 | " | " | 4-CF₃-C₆H₄- | |
| 220 | " | " | 4-CN-C₆H₄- | |
| 221 | " | " | 4-NO₂-C₆H₄- | |
| 222 | " | -CH(CH₃)C≡CH | 2-Cl-C₆H₄- | |
| 223 | " | " | 3-Cl-C₆H₄- | |
| 224 | " | " | 4-Cl-C₆H₄- | |
| 225 | " | " | 4-Br-C₆H₄- | |
| 226 | " | " | 4-F-C₆H₄- | |
| 227 | " | " | 4-CH₃-C₆H₄- | |
| 228 | " | C₆H₅- | -CH₂-(epoxide) | |
| 229 | " | -C(CH₃)₂C≡CH | 4-Cl-3-F-C₆H₃- | |
| 230 | " | " | 3-F-C₆H₄- | |

TABLE 1-continued $$\text{Xn} - \triangle - \underset{\underset{N = N}{N - N}}{N} - \overset{O}{\underset{}{C}} - \underset{\underset{}{N - C}}{N} - \overset{O}{\underset{}{C}} - N \overset{R^1}{\underset{R^2}{}} \quad (I)$$

| Compound No. | $X_a$ | $R^1$ | $R^2$ | physical property |
|---|---|---|---|---|
| 231 | " | " | 3-F-C₆H₄ | |
| 232 | " | " | 4-F-C₆H₄ | |
| 233 | " | —CH(CH₃)C≡CH | 4-F-C₆H₄ | |
| 234 | 2-CH₃ | —CH(CH₃)C≡CH | 2-F-C₆H₄ | |
| 235 | " | " | 3-F-C₆H₄ | |
| 236 | " | C₃H₇-i | —CH₂-(2-Cl-C₆H₄) | |
| 237 | " | " | —CH₂-(4-Cl-C₆H₄) | |
| 238 | " | " | —CH(CH₃)-(4-Cl-C₆H₄) | |
| 239 | " | " | —CH₂-(4-F-C₆H₄) | |
| 240 | " | " | —CH₂-(2-F-C₆H₄) | |
| 241 | " | " | —CH₂-(3-CH₃-C₆H₄) | |

TABLE 1-continued
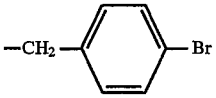
| Compound No. | $X_a$ | $R^1$ | $R^2$ | physical property |
|---|---|---|---|---|
| 242 | " | " | 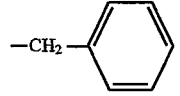 | |
| 243 | " | —C(CH$_3$)$_2$C≡CH | 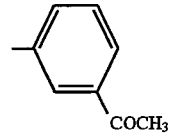 | |
| 244 | " | C$_3$H$_7$-i | 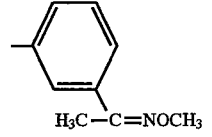 | |
| 245 | " | " | 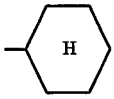 | |
| 246 | " | " | 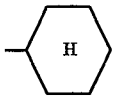 | |
| 247 | 1,2-(CH$_3$)$_2$ | C$_2$H$_5$ | C$_2$H$_5$ | |
| 248 | " | " |  | |
| 249 | 1,2-(CH$_3$)$_2$ | C$_3$H$_7$-n | C$_3$H$_7$-n | |
| 250 | " | " |  | |
| 251 | " | " | 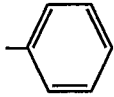 | |
| 252 | " | C$_3$H$_7$-i | 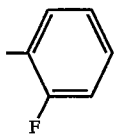 | |
| 253 | " | " | | |
| 254 | " | " | 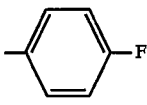 | |

TABLE 1-continued
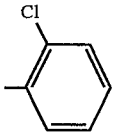
| Compound No. | $X_a$ | $R^1$ | $R^2$ | physical property |
|---|---|---|---|---|
| 255 | " | " | 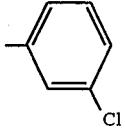 2-Cl-phenyl | |
| 256 | " | " | 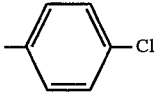 3-Cl-phenyl | |
| 257 | " | " | 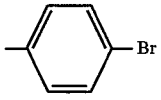 4-Cl-phenyl | |
| 258 | " | " | 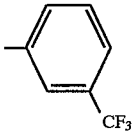 4-Br-phenyl | |
| 259 | " | " | 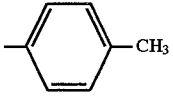 3-CF$_3$-phenyl | |
| 260 | " | " | 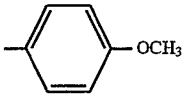 4-CH$_3$-phenyl | |
| 261 | " | " | 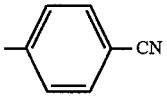 4-OCH$_3$-phenyl | |
| 262 | " | " |  4-CN-phenyl | |
| 263 | " | —CH(CH$_3$)—CH$_2$CH$_2$— | 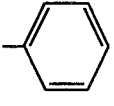 2-methylphenyl | |
| 264 | " | —C(CH$_3$)$_2$C≡CH | 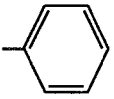 phenyl | |
| 265 | 1,2-(CH$_3$)$_2$ | —CH(CH$_3$)C≡CH | phenyl | |
| 266 | " | C$_3$H$_7$-i | —CH$_2$— 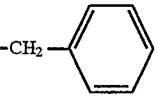 phenyl | |

TABLE 1-continued
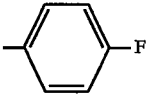
| Compound No. | $X_a$ | $R^1$ | $R^2$ | physical property |
|---|---|---|---|---|
| 267 | " | —C(CH₃)₂C≡CH | 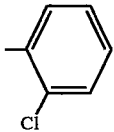 4-F-C₆H₄ | |
| 268 | " | " | 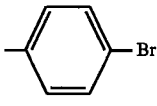 2-Cl-C₆H₄ | |
| 269 | " | " | 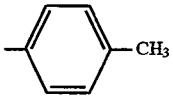 4-Br-C₆H₄ | |
| 270 | " | $C_3H_7$-i | 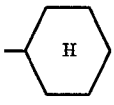 4-CH₃-C₆H₄ | |
| 271 | 2,3-(CH₃)₂ | $C_2H_5$ | $C_2H_5$ | |
| 272 | " | " |  cyclohexyl | |
| 273 | " | $C_3H_7$-n | $C_3H_7$-n | |
| 274 | " | " |  cyclopropyl | |
| 275 | " | " | 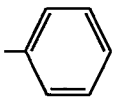 cyclopentyl | |
| 276 | " | $C_3H_7$-i | 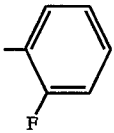 C₆H₅ | |
| 277 | " | " | 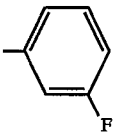 2-F-C₆H₄ | |
| 278 | " | " | 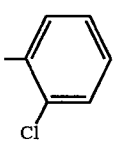 3-F-C₆H₄ | |
| 279 | " | " | 3-Cl-C₆H₄ | |

TABLE 1-continued $$Xn-\triangleleft-\underset{N=N}{N-\underset{O}{\overset{O}{C}}-N-\underset{O}{\overset{O}{C}}-N<\underset{R^2}{R^1}} \quad (I)$$

| Compound No. | $X_a$ | $R^1$ | $R^2$ | physical property |
|---|---|---|---|---|
| 280 | " | " | 4-Cl-C₆H₄ | |
| 281 | 2,3-(CH₃)₂ | C₃H₇-i | 3-Cl-C₆H₄ | |
| 282 | " | " | 4-Br-C₆H₄ | |
| 283 | " | " | 4-CF₃-C₆H₄ | |
| 284 | " | " | 2-CH₃-C₆H₄ | |
| 285 | " | " | 2-OCH₃-C₆H₄ | |
| 286 | " | " | 4-NO₂-C₆H₄ | |
| 287 | " | —CH(CH₃)—CH₂CH₂— | 2-CH₃-C₆H₄ | |
| 288 | " | —C(CH₃)₂C≡CH | C₆H₅ | |
| 289 | " | " | 3-F-C₆H₄ | |
| 290 | " | " | 4-F-C₆H₄ | |
| 291 | " | " | 4-Br-C₆H₄ | |

TABLE 1-continued $$Xn-\text{cyclopropyl}-N(-C(=O)-N(-C(=O)-N(R^1)(R^2))-N=N \text{ (tetrazole ring)} \quad (I)$$

| Compound No. | $X_a$ | $R^1$ | $R^2$ | physical property |
|---|---|---|---|---|
| 292 | " | " | 4-methylphenyl | |
| 293 | " | —CH(CH$_3$)C≡CH | phenyl | |
| 294 | " | C$_3$H$_7$-i | cyclohexyl | |
| 295 | 2,2-(CH$_3$)$_2$ | C$_2$H$_5$ | C$_2$H$_5$ | |
| 296 | " | " | cyclohexyl | |
| 297 | 2,2-(CH$_3$)$_2$ | C$_3$H$_7$-n | C$_3$H$_7$-n | |
| 298 | " | " | cyclopropyl | |
| 299 | " | " | cyclohexyl | |
| 300 | " | C$_3$H$_7$-i | phenyl | |
| 301 | " | " | 2-F-phenyl | |
| 302 | " | " | 4-F-phenyl | |
| 303 | " | " | 2-Cl-phenyl | |
| 304 | " | " | 3-Cl-phenyl | |

TABLE 1-continued $$Xn-\triangle-N(-C(=O)-N-C(=O)-N(R^1)(R^2))-N=N \quad (I)$$

| Compound No. | $X_n$ | $R^1$ | $R^2$ | physical property |
|---|---|---|---|---|
| 305 | " | " | 4-Br-C₆H₄— | |
| 306 | " | " | 4-CF₃-C₆H₄— | |
| 307 | " | " | 3,5-Cl₂-C₆H₃— | |
| 308 | " | " | 4-OCH₃-C₆H₄— | |
| 309 | " | " | 4-CN-C₆H₄— | |
| 310 | " | " | —CH(CH₃)—CH₂CH₂-(2-CH₃-C₆H₄) | |
| 311 | " | —C(CH₃)₂C≡CH | C₆H₅— | |
| 312 | " | " | 4-Br-C₆H₄— | |
| 313 | 2,2-(CH₃)₂ | —C(CH₃)₂C≡CH | 4-Cl-C₆H₄— | |
| 314 | " | " | 4-F-C₆H₄— | |
| 315 | " | " | 2-F-C₆H₄— | |
| 316 | " | —C(CH₃)₂C≡CH | C₆H₅— | |

TABLE 1-continued
| Compound No. | $X_a$ | $R^1$ | $R^2$ | physical property |
|---|---|---|---|---|
| 317 | " | " | 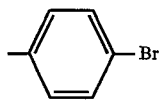—Br | |
| 318 | 1,2,2-$(CH_3)_3$ | $C_2H_5$ | $C_2H_5$ | |
| 319 | " | " | 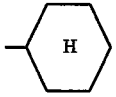—H | |
| 320 | " | $C_3H_7$-n | $C_3H_7$-n | |
| 321 | " | " |  | |
| 322 | " | " | —H | |
| 323 | " | $C_3H_7$-i | 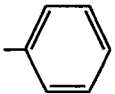 | |
| 324 | " | " | 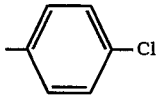—Cl | |
| 325 | " | —$C(CH_3)_2C\equiv CH$ | 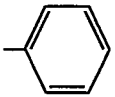 | |
| 326 | 1,2,3-$(CH_3)_3$ | $C_2H_5$ | $C_2H_5$ | |
| 327 | " | " | 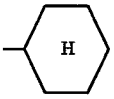—H | |
| 328 | " | $C_3H_7$-n | $C_3H_7$-n | |
| 329 | " | " |  | |
| 330 | " | " | —H | |
| 331 | 1,2,3-$(CH_3)_3$ | $C_3H_7$-i | 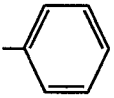 | |
| 332 | " | " | 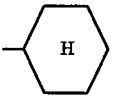—H | |

TABLE 1-continued
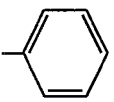
(I)
| Compound No. | $X_a$ | $R^1$ | $R^2$ | physical property |
|---|---|---|---|---|
| 333 | " | —C(CH$_3$)$_2$C≡CH | 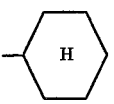 | |
| 334 | 1,2,2,3,3-(CH$_3$)$_5$ | C$_2$H$_5$ | C$_2$H$_5$ | |
| 335 | " | " |  | mp. 103~109° C. |
| 336 | " | C$_3$H$_7$-n | C$_3$H$_7$-n | |
| 337 | " | " |  | |
| 338 | " | " | 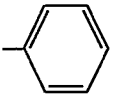 | |
| 339 | " | C$_3$H$_7$-i | 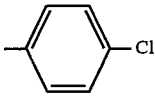 | $n_D^{20}$ 1.5176 |
| 340 | " | " | 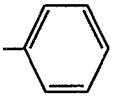 | |
| 341 | " | —C(CH$_3$)$_2$C≡CH | 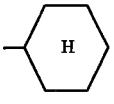 | |
| 342 | 1-C$_2$H$_5$ | C$_2$H$_5$ | C$_2$H$_5$ | |
| 343 | " | " |  | |
| 344 | " | C$_3$H$_7$-n | C$_3$H$_7$-n | |
| 345 | " | " |  | |
| 346 | " | C$_3$H$_7$-n | 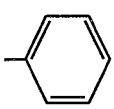 | |
| 347 | " | C$_3$H$_7$-i | 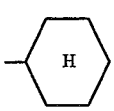 | |
| 348 | " | " |  | |

TABLE 1-continued
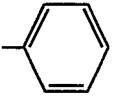
| Compound No. | $X_a$ | $R^1$ | $R^2$ | physical property |
|---|---|---|---|---|
| 349 | " | —C(CH$_3$)$_2$C≡CH | 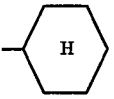 | |
| 350 | 2-C$_2$H$_5$ | C$_2$H$_5$ | C$_2$H$_5$ | |
| 351 | " | " |  | |
| 352 | " | C$_3$H$_7$-n | C$_3$H$_7$-n | |
| 353 | " | " |  | |
| 354 | " | " | 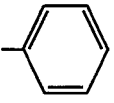 | |
| 355 | " | C$_3$H$_7$-i | 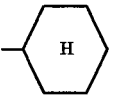 | |
| 356 | " | " | 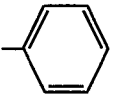 | |
| 357 | " | —C(CH$_3$)$_2$C≡CH | 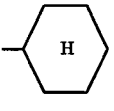 | |
| 358 | 1-C$_2$H$_5$, 2-CH$_3$ | C$_2$H$_5$ | C$_2$H$_5$ | |
| 359 | " | " |  | |
| 360 | " | C$_3$H$_7$-n | C$_3$H$_7$-n | |
| 361 | " | " |  | |
| 362 | " | " | 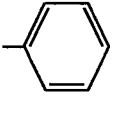 | |
| 363 | " | C$_3$H$_7$-i | 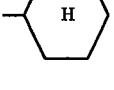 | |
| 364 | " | " |  | |

TABLE 1-continued (I)
Xn—△—N—C(=O)—N—C(=O)—N(R¹)(R²) with tetrazole ring (N=N)

| Compound No. | X_a | R¹ | R² | physical property |
|---|---|---|---|---|
| 365 | " | —C(CH₃)₂C≡CH | phenyl | |
| 366 | 2-C₂H₅, 3-CH₃ | C₂H₅ | C₂H₅ | |
| 367 | " | " | cyclohexyl | |
| 368 | " | C₃H₇-i | phenyl | |
| 369 | 2-C₃H₇-n | C₂H₅ | cyclohexyl | |
| 370 | " | C₃H₇-i | phenyl | |
| 371 | 2-C₃H₇-i | C₂H₅ | cyclohexyl | |
| 372 | " | C₃H₇-i | phenyl | |
| 373 | " | " | 2-F-phenyl | |
| 374 | 1-C₃H₇-i | C₂H₅ | C₂H₅ | |
| 375 | " | " | cyclohexyl | |
| 376 | " | C₃H₇-i | phenyl | |
| 377 | 2,2-(CH₃)₂, 3-CH=CH₂ | C₂H₅ | cyclohexyl | |
| 378 | " | C₃H₇-i | phenyl | |

TABLE 1-continued $$Xn-\triangle-N(-N=N-N(-C(=O)-N(-C(=O)-NR^1R^2)))$$ (I)

| Compound No. | $X_a$ | $R^1$ | $R^2$ | physical property |
|---|---|---|---|---|
| 379 | 2,2-$(CH_3)_2$, 3-$CH=C(CH_3)_2$ | $C_2H_5$ | cyclohexyl | $n_D^{20}$ 1.5060 |
| 380 | 2,2-$(CH_3)_2$, 3-$CH=C(CH_3)_2$ | $C_3H_7$-i | phenyl | mp. 110~111.5° C. |
| 381 | 2,2-$Cl_2$ | $C_2H_5$ | $C_2H_5$ | $n_D^{20}$ 1.5052 |
| 382 | " | " | cyclohexyl | $n_D^{20}$ 1.5163 |
| 383 | " | $C_3H_7$-n | $C_3H_7$-n | |
| 384 | " | " | cyclopropyl | |
| 385 | " | " | cyclopentyl | |
| 386 | " | $-CH_2CH=CH_2$ | $-CH_2CH=CH_2$ | |
| 387 | 2,2-$Cl_2$ | $C_3H_7$-i | phenyl | mp. 131~134° C. |
| 388 | " | " | 2-F-phenyl | |
| 389 | " | " | 4-F-phenyl | |
| 390 | " | " | 2-Cl-phenyl | |
| 391 | " | " | 3-Cl-phenyl | |
| 392 | " | " | 4-Cl-phenyl | |

TABLE 1-continued
| Compound No. | $X_a$ | $R^1$ | $R^2$ | physical property |
|---|---|---|---|---|
| 393 | " | " | 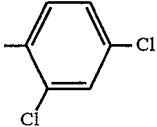 2,4-Cl$_2$-C$_6$H$_3$ | |
| 394 | " | " | 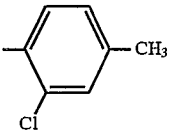 3-Cl-4-CH$_3$-C$_6$H$_3$ | |
| 395 | " | " | 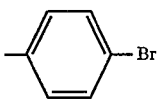 4-Br-C$_6$H$_4$ | |
| 396 | " | " | 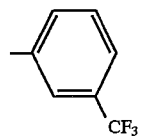 3-CF$_3$-C$_6$H$_4$ | |
| 397 | " | " | 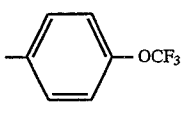 4-OCF$_3$-C$_6$H$_4$ | |
| 398 | " | " | 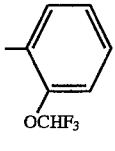 2-OCHF$_2$-C$_6$H$_4$ | |
| 399 | " | " | 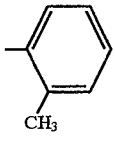 2-CH$_3$-C$_6$H$_4$ | |
| 400 | " | " | 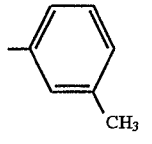 3-CH$_3$-C$_6$H$_4$ | |
| 401 | 2,2-Cl$_2$ | C$_3$H$_7$-i | 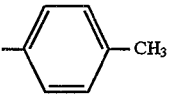 4-CH$_3$-C$_6$H$_4$ | |
| 402 | " | " | 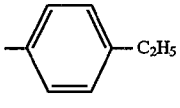 4-C$_2$H$_5$-C$_6$H$_4$ | |
| 403 | " | " | 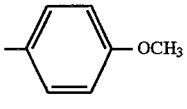 4-OCH$_3$-C$_6$H$_4$ | |

TABLE 1-continued $$Xn-\triangleleft-N(-N=N-N(-C(=O)-C(=O)-NR^1R^2))\quad (I)$$

| Compound No. | $X_a$ | $R^1$ | $R^2$ | physical property |
|---|---|---|---|---|
| 404 | " | " | 4-$NO_2$-$C_6H_4$- | |
| 405 | " | " | 4-CN-$C_6H_4$- | |
| 406 | " | —(CH$_2$)$_4$— | | |
| 407 | " | —(CH$_2$)$_3$—CH(CH$_3$)— | | |
| 408 | " | —(CH$_2$)$_2$-(2-CH$_3$-C$_6$H$_4$)— | | |
| 409 | " | —(CH$_2$)$_3$-(2-CH$_3$-C$_6$H$_4$)— | | |
| 410 | " | —CH(CH$_3$)—CH$_2$-(2-CH$_3$-C$_6$H$_4$)— | | |
| 411 | " | —C(CH$_3$)$_2$C≡CH | C$_6$H$_5$- | |
| 412 | " | —CH(CH$_3$)C≡CH | C$_6$H$_5$- | |
| 413 | " | —CH$_2$C≡CH | C$_6$H$_5$- | |
| 414 | " | —CH$_2$CH=CH$_2$ | C$_6$H$_5$- | |
| 415 | " | C$_3$H$_7$-i | —CH$_2$-C$_6$H$_5$ | |
| 416 | " | C$_3$H$_7$-n | C$_6$H$_5$- | |
| 417 | " | CH$_3$ | " | |
| 418 | 2,2-Cl$_2$ | C$_2$H$_5$ | C$_6$H$_5$- | |
| 419 | " | C$_4$H$_9$-n | " | |

TABLE 1-continued

| Compound No. | $X_a$ | $R^1$ | $R^2$ | physical property |
|---|---|---|---|---|
| 420 | " | $C_4H_9$-sec | " | |
| 421 | " | $C_4H_9$-i | " | |
| 422 | " | $-C(CH_3)_2C\equiv CH$ | 2-Cl-C6H4 | |
| 423 | " | " | 3-Cl-C6H4 | |
| 424 | " | " | 4-Cl-C6H4 | |
| 425 | " | " | 2-Br-C6H4 | |
| 426 | " | " | 4-Br-C6H4 | |
| 427 | " | " | 4-CH3-C6H4 | |
| 428 | " | " | 4-CF3-C6H4 | |
| 429 | " | " | 4-CN-C6H4 | |
| 430 | " | " | 4-NO2-C6H4 | |
| 431 | " | $-CH(CH_3)C\equiv CH$ | 3-Cl-C6H4 | |

TABLE 1-continued

[Structure (I): Xn-cyclopropyl-N(C=O)N-N=N with C(=O)-N(R¹)(R²)]

| Compound No. | $X_a$ | $R^1$ | $R^2$ | physical property |
|---|---|---|---|---|
| 432 | " | " | 3-Cl-phenyl | |
| 433 | " | " | 4-Cl-phenyl | |
| 434 | 2,2-Cl$_2$ | —CH(CH$_3$)C≡CH | 4-Br-phenyl | |
| 435 | " | " | 4-F-phenyl | |
| 436 | " | phenyl | —CH$_2$-(epoxide) | |
| 437 | " | —C(CH$_3$)$_2$C≡CH | 3-F,4-Cl-phenyl | |
| 438 | " | " | 2-F-phenyl | |
| 439 | " | " | 3-F-phenyl | |
| 440 | " | " | 4-F-phenyl | |
| 441 | " | —CH(CH$_3$)C≡CH | 4-F-phenyl | |
| 442 | " | " | 2-F-phenyl | |

TABLE 1-continued

Structure (I): Xn—(cyclopropyl)—N(—N=N—N—)—C(=O)—N—C(=O)—N(R¹)(R²)

| Compound No. | $X_a$ | R¹ | R² | physical property |
|---|---|---|---|---|
| 443 | " | " | 3-fluorophenyl | |
| 444 | " | $C_3H_7$-i | —$CH_2$—(2-chlorophenyl) | |
| 445 | " | " | —$CH_2$—(4-chlorophenyl) | |
| 446 | " | " | —$CH(CH_3)$—(4-chlorophenyl) | |
| 447 | " | " | —$CH_2$—(4-fluorophenyl) | |
| 448 | " | " | —$CH_2$—(2-fluorophenyl) | |
| 449 | 2,2-$Cl_2$ | $C_3H_7$-i | —$CH_2$—(2-methylphenyl, with $CH_2$) | |
| 450 | " | " | —$CH_2$—(4-bromophenyl) | |
| 451 | " | —$C(CH_3)_2C\equiv CH$ | —$CH_2$—phenyl | |
| 452 | " | $C_3H_7$-i | 3-($COCH_3$)phenyl | |
| 453 | 2,2-$Cl_2$, 1-$CH_3$ | $C_2H_5$ | $C_3H_7$-i | $n_D^{20}$ 1.5003 |
| 454 | " | " | cyclohexyl | |
| 455 | 2,2-$Br_2$ | " | $C_2H_5$ | |

TABLE 1-continued $$Xn\text{-}\triangle\text{-}N\text{-}C(=O)\text{-}N\text{-}C(=O)\text{-}N(R^1)(R^2) \quad (I)$$
(with N=N in ring)

| Compound No. | $X_a$ | $R^1$ | $R^2$ | physical property |
|---|---|---|---|---|
| 456 | " | " | cyclohexyl-H | |
| 457 | " | $C_3H_7$-n | $C_3H_7$-n | |
| 458 | " | " | cyclopropyl | |
| 459 | " | " | cyclopentyl-H | |
| 460 | " | $C_3H_7$-i | phenyl | |
| 461 | " | " | cyclohexyl-H | |
| 462 | " | $-C(CH_3)_2C\equiv CH$ | phenyl | |
| 463 | 2,2-$F_2$ | $C_2H_5$ | $C_2H_5$ | |
| 464 | " | " | cyclohexyl-H | |
| 465 | " | $C_3H_7$-n | $C_3H_7$-n | |
| 466 | 2,2-$F_2$ | $C_3H_7$-n | cyclopropyl | |
| 467 | " | " | cyclopentyl-H | |
| 468 | " | $C_3H_7$-i | phenyl | $n_D^{20}$ 1.5047 |
| 469 | " | " | cyclohexyl-H | |
| 470 | " | $-C(CH_3)_2C\equiv CH$ | phenyl | |
| 471 | 2,2-$Cl_2$, 1-$CH_3$ | $C_2H_5$ | $C_2H_5$ | $n_D^{20}$ 1.5072 |

TABLE 1-continued (I) structure: Xn-cyclopropyl-N-C(=O)-N(tetrazole)-N-C(=O)-N(R¹)(R²)

| Compound No. | $X_a$ | R¹ | R² | physical property |
|---|---|---|---|---|
| 472 | " | " | cyclohexyl-H | $n_D^{20}$ 1.5068 |
| 473 | " | $C_3H_7$-n | $C_3H_7$-n | |
| 474 | " | " | cyclopropyl | |
| 475 | " | " | cyclopentyl-H | |
| 476 | " | $C_3H_7$-i | phenyl | $n_D^{20}$ 1.5328 |
| 477 | " | " | cyclohexyl-H | |
| 478 | " | $-C(CH_3)_2C{\equiv}CH$ | phenyl | |
| 479 | 2,2-$Cl_2$, 1,3-$(CH_3)_2$ | $C_2H_5$ | $C_2H_5$ | $n_D^{20}$ 1.5048 |
| 480 | " | " | cyclohexyl-H | $n_D^{20}$ 1.5276 |
| 481 | " | $C_3H_7$-n | $C_3H_7$-n | |
| 482 | " | " | cyclopropyl | |
| 483 | " | " | cyclopentyl-H | |
| 484 | 2,2-$Cl_2$, 1,3-$(CH_3)_2$ | $C_3H_7$-i | phenyl | $n_D^{20}$ 1.5223 |
| 485 | " | " | cyclohexyl-H | |
| 486 | " | $-C(CH_3)_2C{\equiv}CH$ | phenyl | |
| 487 | 2,2-$F_2$, 1-$CH_3$ | $C_2H_5$ | $C_2H_5$ | $n_D^{20}$ 1.4653 |

TABLE 1-continued $$Xn-\triangle-N-\overset{O}{\underset{N=N}{C}}-N-\overset{O}{C}-N\overset{R^1}{\underset{R^2}{}} \quad (I)$$

| Compound No. | $X_a$ | $R^1$ | $R^2$ | physical property |
|---|---|---|---|---|
| 488 | " | " | —⌬H (cyclohexyl) | $n_D^{20}$ 1.4797 |
| 489 | " | $C_3H_7$-n | $C_3H_7$-n | |
| 490 | " | " | —▷ (cyclopropyl) | |
| 491 | " | " | —⬠H (cyclopentyl) | |
| 492 | " | $C_3H_7$-i | —⌬ (phenyl) | $n_D^{20}$ 1.5083 |
| 493 | " | " | —⌬H (cyclohexyl) | |
| 494 | " | —C(CH$_3$)$_2$C≡CH | —⌬ (phenyl) | |
| 495 | 2,2-Cl$_2$, 3-CH$_3$ | $C_2H_5$ | $C_2H_5$ | |
| 496 | " | " | —⌬H (cyclohexyl) | |
| 497 | " | $C_3H_7$-n | $C_3H_7$-n | |
| 498 | " | " | —▷ (cyclopropyl) | |
| 499 | " | " | —⬠H (cyclopentyl) | |
| 500 | " | $C_3H_7$-i | —⌬ (phenyl) | |
| 501 | " | " | —⌬H (cyclohexyl) | |
| 502 | 2,2-Cl$_2$, 3-CH$_3$ | —C(CH$_3$)$_2$C≡CH | —⌬ (phenyl) | |
| 503 | 2,2-Cl$_2$, 1,3,3-(CH$_3$)$_3$ | $C_2H_5$ | $C_2H_5$ | $n_D^{20}$ 1.5016 |

TABLE 1-continued $$Xn-\triangle-\underset{N-N}{N}-\overset{O}{\overset{\|}{C}}-\underset{N-N}{N}-\overset{O}{\overset{\|}{C}}-N\overset{R^1}{\underset{R^2}{}}\quad (I)$$

| Compound No. | $X_a$ | $R^1$ | $R^2$ | physical property |
|---|---|---|---|---|
| 504 | " | " | cyclohexyl-H | |
| 505 | " | $C_3H_7$-n | $C_3H_7$-n | |
| 506 | " | " | cyclopropyl | |
| 507 | " | " | cyclopentyl-H | |
| 508 | " | $C_3H_7$-i | phenyl | |
| 509 | " | " | cyclohexyl-H | |
| 510 | " | $-C(CH_3)_2C\equiv CH$ | phenyl | |
| 511 | 2,2-$Cl_2$, 1-$C_2H_5$ | $C_2H_5$ | $C_2H_5$ | |
| 512 | " | " | cyclohexyl-H | |
| 513 | " | $C_3H_7$-n | $C_3H_7$-n | |
| 514 | " | " | cyclopropyl | |
| 515 | " | " | cyclopentyl-H | |
| 516 | " | $C_3H_7$-i | phenyl | |
| 517 | " | " | cyclohexyl-H | |
| 518 | " | $-C(CH_3)_2C\equiv CH$ | phenyl | |
| 519 | 2-Cl, 2-F | $C_2H_5$ | cyclohexyl-H | |

TABLE 1-continued
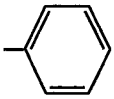
| Compound No. | $X_a$ | $R^1$ | $R^2$ | physical property |
|---|---|---|---|---|
| 520 | 2-Cl, 2-F | $C_3H_7$-i | 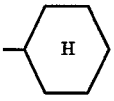 | $n_D^{20}$ 1.5194 |
| 521 | 2-Cl, 2-F, 1-CH$_3$ | $C_2H_5$ | 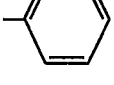 H | |
| 522 | " | $C_3H_7$-i | 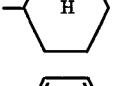 | |
| 523 | 2,2-Br$_2$, 1-CH$_3$ | $C_2H_5$ | 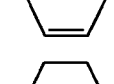 H | |
| 524 | " | $C_3H_7$-i | 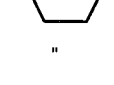 | |
| 525 | 2,2-Br$_2$, 1,3-(CH$_3$)$_2$ | $C_2H_5$ | 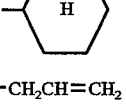 H | |
| 526 | 2,2-Cl$_2$, 1-C$_2$H$_5$, 3-CH$_3$ | " | " | |
| 527 | 2,2-Cl$_2$, 1-C$_3$H$_7$-i | $C_3H_7$-i | 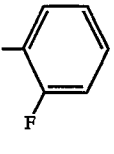 H | |
| 528 | 2,2-F$_2$ | —CH$_2$CH=CH$_2$ | —CH$_2$CH=CH$_2$ | |
| 529 | " | —CH$_2$C≡CH | —CH$_2$C≡CH | |
| 530 | " | $C_3H_7$-i | 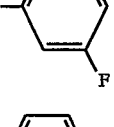 F | |
| 531 | " | " | 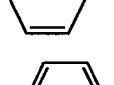 F | |
| 532 | " | " | 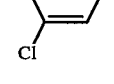 F | $n_D^{20}$ 1.4996 |
| 533 | " | " |  Cl | |

TABLE 1-continued
(I) [structure shown]
| Compound No. | $X_a$ | $R^1$ | $R^2$ | physical property |
|---|---|---|---|---|
| 534 | " | " | 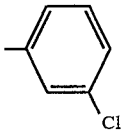 3-Cl-phenyl | |
| 535 | " | " | 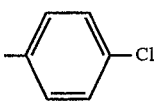 4-Cl-phenyl | $n_D^{20}$ 1.5203 |
| 536 | 2,2-$F_2$ | $C_3H_7$-i | 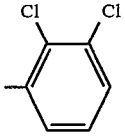 2,3-Cl$_2$-phenyl | |
| 537 | " | " | 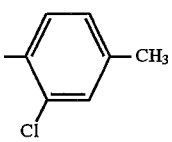 3-Cl-4-CH$_3$-phenyl | |
| 538 | " | " | 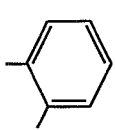 2-Br-phenyl | |
| 539 | " | " | 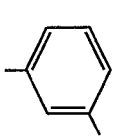 3-Br-phenyl | |
| 540 | " | " | 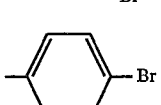 4-Br-phenyl | |
| 541 | " | " | 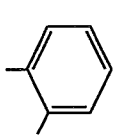 2-CF$_3$-phenyl | |
| 542 | " | " | 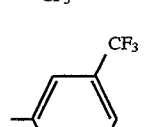 3-CF$_3$-phenyl | |
| 543 | " | " | 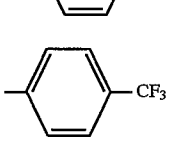 4-CF$_3$-phenyl | |

TABLE 1-continued
(I) Xn—[cyclopropyl]—N(C=O)—N—C(=O)—N(R¹)(R²), with N=N in ring
| Compound No. | X_a | R¹ | R² | physical property |
|---|---|---|---|---|
| 544 | " | " | 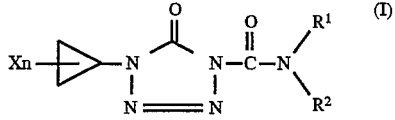 4-OCH₃-C₆H₄- | |
| 545 | " | " | 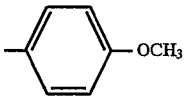 4-OCHF₂-C₆H₄- | |
| 546 | " | " | 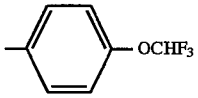 4-SCF₃-C₆H₄- | |
| 547 | " | " | 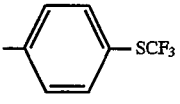 4-CH₃-C₆H₄- | |
| 548 | " | " | 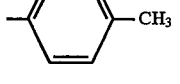 3-CH₃-C₆H₄- | |
| 549 | " | " | 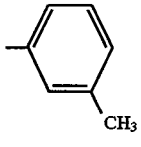 2-CH₃-C₆H₄- | |
| 550 | 2,2-F₂ | C₃H₇-i | 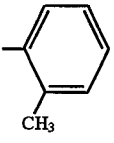 2,4-(CH₃)₂-C₆H₃- | |
| 551 | " | " | 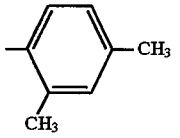 2-C₂H₅-C₆H₄- | |
| 552 | " | " | 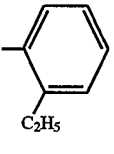 4-NO₂-C₆H₄- | |
| 553 | " | " | 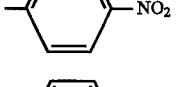 4-CN-C₆H₄- | |
| 554 | " | —(CH₂)₄— | | |
| 555 | " | —(CH₂)₃—CH(CH₃)— | | |
| 556 | " | | 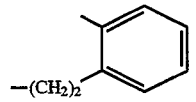 —(CH₂)₂-(2-CH₃-C₆H₄)- | |

TABLE 1-continued
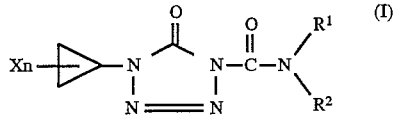
(I)
| Compound No. | $X_a$ | $R^1$ | $R^2$ | physical property |
|---|---|---|---|---|
| 557 | " | —(CH₂)₃— 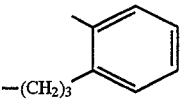 | | |
| 558 | " | —CH(CH₃)—CH₂CH₂— 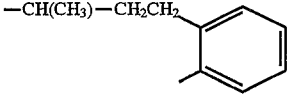 | | $n_D^{20}$ 1.5343 |
| 559 | " | —CH(CH₃)C≡CH | 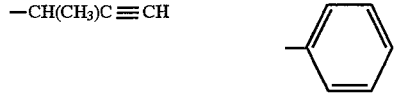 | |
| 560 | " | —CH₂C≡CH | " | |
| 561 | " | C₃H₇-i | —CH₂— 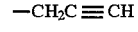 | |
| 562 | " | C₃H₇-n | 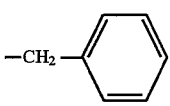 | |
| 563 | " | CH₃ | " | |
| 564 | " | C₂H₅ | " | $n_D^{20}$ 1.5188 |
| 565 | " | C₄H₉-n | " | |
| 566 | 2,2-F₂ | C₄H₉-sec | 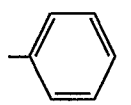 | |
| 567 | " | C₄H₉-i | " | |
| 568 | " |  | " | |
| 569 | " | —C(CH₃)₂C≡CH |  | |
| 570 | " | " |  | |
| 571 | " | " | 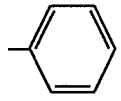 | |

TABLE 1-continued
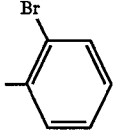
| Compound No. | $X_a$ | $R^1$ | $R^2$ | physical property |
|---|---|---|---|---|
| 572 | " | " | 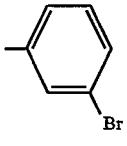 2-Br-C6H4 | |
| 573 | " | " | 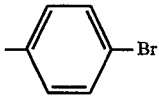 3-Br-C6H4 | |
| 574 | " | " | 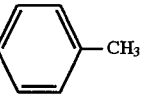 4-Br-C6H4 | |
| 575 | " | " | 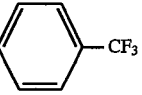 4-CH3-C6H4 | |
| 576 | " | " | 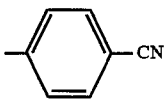 4-CF3-C6H4 | |
| 577 | " | " | 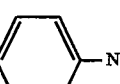 4-CN-C6H4 | |
| 578 | " | " | 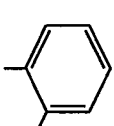 4-NO2-C6H4 | |
| 579 | " | —CH(CH3)C≡CH | 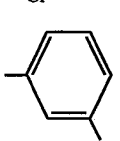 2-Cl-C6H4 | |
| 580 | " | " | 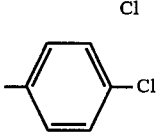 3-Cl-C6H4 | |
| 581 | " | " | 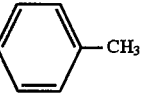 4-Cl-C6H4 | |
| 582 | 2,2-F2 | —CH(CH3)C≡CH | 4-CH3-C6H4 | |
| 583 | " | " | 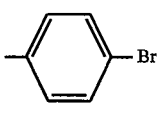 4-Br-C6H4 | |

TABLE 1-continued
| Compound No. | $X_a$ | $R^1$ | $R^2$ | physical property |
|---|---|---|---|---|
| 584 | " | " | 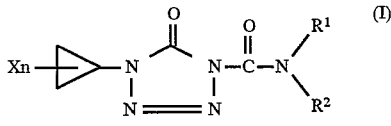 3,5-diCl-phenyl | |
| 585 | " | —C(CH₃)₂C≡CH | 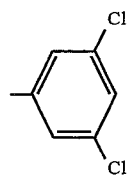 4-F-phenyl | |
| 586 | " | " | 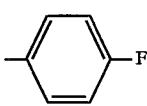 2-F-phenyl | |
| 587 | " | —CH(CH₃)C≡CH | 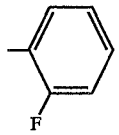 4-F-phenyl | |
| 588 | " | " | 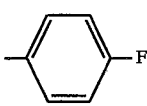 3-F-phenyl | |
| 589 | " | " | 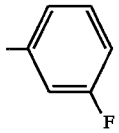 2-F-phenyl | |
| 590 | " | $C_3H_7$-i | —CH₂—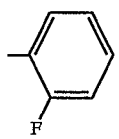 2-Cl-phenyl | |
| 591 | " | " | —CH₂—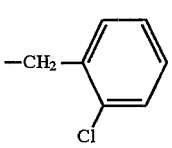 3-Cl-phenyl | |
| 592 | " | " | —CH₂—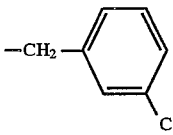 4-Cl-phenyl | |
| 593 | " | " | —CH(CH₃)—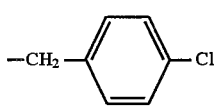 phenyl | |

TABLE 1-continued

Structure (I):
Xn—(cyclopropyl)—N(—N=N—N=)—C(=O)—N—C(=O)—NR¹R²

| Compound No. | $X_a$ | $R^1$ | $R^2$ | physical property |
|---|---|---|---|---|
| 594 | " | " | —CH$_2$—C$_6$H$_4$—F (4-) | |
| 595 | " | " | —CH$_2$—C$_6$H$_4$—F (2-) | |
| 596 | " | " | —CH$_2$—C$_6$H$_4$—CH$_3$ (4-) | |
| 597 | 2,2-F$_2$ | C$_3$H$_7$-i | —CH$_2$—C$_6$H$_4$—Br (4-) | |
| 598 | " | " | —CH$_2$—C$_6$H$_4$—NO$_2$ (4-) | |
| 599 | " | " | —CH$_2$—C$_6$H$_3$—Cl$_2$ (2,4-) | |
| 600 | " | " | —CH$_2$—C$_6$H$_4$—CF$_3$ (4-) | |
| 601 | " | —C(CH$_3$)$_2$C≡CH | —CH$_2$—C$_6$H$_5$ | |
| 602 | " | —CH(CH$_3$)C≡CH | " | |
| 603 | 2,2-F$_2$, 1-CH$_3$ | —CH$_2$CH=CH$_2$ | —CH$_2$CH=CH$_2$ | |
| 604 | " | —CH$_2$C≡CH | —CH$_2$C≡CH | |
| 605 | " | C$_3$H$_7$-i | —C$_6$H$_4$—F (2-) | |
| 606 | " | " | —C$_6$H$_4$—F (3-) | |

TABLE 1-continued
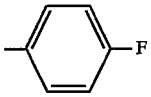
(I)
| Compound No. | $X_a$ | $R^1$ | $R^2$ | physical property |
|---|---|---|---|---|
| 607 | " | " | 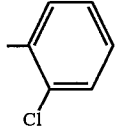 4-F | $n_D^{20}$ 1.4893 |
| 608 | " | " | 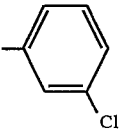 2-Cl | |
| 609 | " | " | 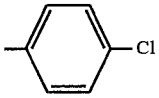 3-Cl | |
| 610 | " | " | 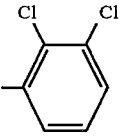 4-Cl | $n_D^{20}$ 1.5095 |
| 611 | " | " | 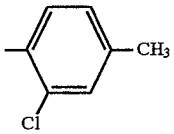 2,3-Cl₂ | |
| 612 | 2,2-F₂, 1-CH₃ | C₃H₇-i | 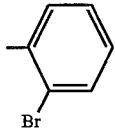 2-Cl, 5-CH₃ | |
| 613 | " | " | 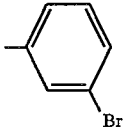 2-Br | |
| 614 | " | " | 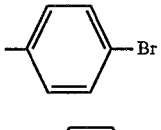 3-Br | |
| 615 | " | " | 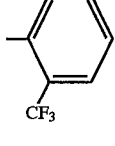 4-Br | |
| 616 | " | " | 2-CF₃ | |

TABLE 1-continued $$\text{Xn}-\triangleleft-\underset{\underset{N=N}{N-}}{\overset{O}{\overset{\|}{C}}}-\underset{\underset{N=N}{N-}}{\overset{O}{\overset{\|}{C}}}-N\underset{R^2}{\overset{R^1}{<}} \quad (I)$$

| Compound No. | $X_a$ | $R^1$ | $R^2$ | physical property |
|---|---|---|---|---|
| 617 | " | " | 3-CF₃-phenyl | |
| 618 | " | " | 4-CF₃-phenyl | |
| 619 | " | " | 4-OCH₃-phenyl | |
| 620 | " | " | 4-OCHF₂-phenyl | |
| 621 | " | " | 4-SCF₃-phenyl | |
| 622 | " | " | 4-CH₃-phenyl | |
| 623 | " | " | 3-CH₃-phenyl | |
| 624 | " | " | 2-CH₃-phenyl | |
| 625 | " | " | 2,4-(CH₃)₂-phenyl | |
| 626 | 2,2-F₂, 1-CH₃ | C₃H₇-i | 2-C₂H₅-phenyl | |
| 627 | " | " | 4-NO₂-phenyl | |

TABLE 1-continued structure (I): Xn-cyclopropyl-N-C(=O)-N-C(=O)-NR¹R² with N=N

| Compound No. | $X_a$ | R¹ | R² | physical property |
|---|---|---|---|---|
| 628 | " | " | -C₆H₄-CN (para) | |
| 629 | " | -(CH₂)₄- | | |
| 630 | " | -(CH₂)₃-CH(CH₃)- | | |
| 631 | " | -(CH₂)₂-(o-C₆H₄-CH₃) | | |
| 632 | " | -(CH₂)₃-(o-C₆H₄-CH₃) | | |
| 633 | " | -CH(CH₃)-CH₂CH₂-(o-C₆H₄-CH₃) | | $n_D^{20}$ 1.5067 |
| 634 | " | -CH(CH₃)C≡CH | phenyl | |
| 635 | " | -CH₂C≡CH | " | |
| 636 | " | C₃H₇-i | -CH₂-phenyl | |
| 637 | " | C₃H₇-n | phenyl | |
| 638 | " | CH₃ | " | |
| 639 | " | C₂H₅ | " | |
| 640 | " | C₄H₉-n | " | |
| 641 | " | C₄H₉-sec | " | |
| 642 | " | C₄H₉-i | " | |
| 643 | 2,2-F₂, 1-CH₃ | phenyl | phenyl | |
| 644 | " | -C(CH₃)₂C≡CH | 2-Cl-phenyl | |

TABLE 1-continued

Structure (I): Xn-cyclopropyl-N-C(O)-N(N=N)-C(O)-N(R¹)(R²)

| Compound No. | X_a | R¹ | R² | physical property |
|---|---|---|---|---|
| 645 | " | " | 3-Cl-phenyl | |
| 646 | " | " | 4-Cl-phenyl | |
| 647 | " | " | 2-Br-phenyl | |
| 648 | " | " | 3-Br-phenyl | |
| 649 | " | " | 4-Br-phenyl | |
| 650 | " | " | 4-CH₃-phenyl | |
| 651 | " | " | 4-CF₃-phenyl | |
| 652 | " | " | 4-CN-phenyl | |
| 653 | " | " | 4-NO₂-phenyl | |
| 654 | " | —CH(CH₃)C≡CH | 2-Cl-phenyl | |
| 655 | " | " | 3-Cl-phenyl | |

TABLE 1-continued (I) Xn-[cyclopropyl]-N(C=O)-N=N-N-C(=O)-N(R¹)(R²)

| Compound No. | $X_a$ | R¹ | R² | physical property |
|---|---|---|---|---|
| 656 | " | " | 4-Cl-phenyl | |
| 657 | " | " | 4-CH₃-phenyl | |
| 658 | " | " | 4-Br-phenyl | |
| 659 | 2,2-F₂, 1-CH₃ | —CH(CH₃)C≡CH | 3,5-diCl-phenyl | |
| 660 | " | —C(CH₃)₂C≡CH | 4-F-phenyl | |
| 661 | " | " | 2-F-phenyl | |
| 662 | " | —CH(CH₃)C≡CH | 4-F-phenyl | |
| 663 | " | " | 3-F-phenyl | |
| 664 | " | " | 2-F-phenyl | |
| 665 | " | C₃H₇-i | —CH₂(2-Cl-phenyl) | |
| 666 | " | " | —CH₂(3-Cl-phenyl) | |

TABLE 1-continued

Structure (I): Xn—[cyclopropyl]—N—C(=O)—N(—C(=O)—NR¹R²)—N=N (tetrazinone)

| Compound No. | X_a | R¹ | R² | physical property |
|---|---|---|---|---|
| 667 | " | " | —CH₂—C₆H₄—Cl (4-Cl) | |
| 668 | " | " | —CH(CH₃)—C₆H₅ | |
| 669 | " | " | —CH₂—C₆H₄—F (4-F) | |
| 670 | " | " | —CH₂—C₆H₄—F (2-F) | |
| 671 | " | " | —CH₂—C₆H₄—CH₃ (4-CH₃) | |
| 672 | " | " | —CH₂—C₆H₄—Br (4-Br) | |
| 673 | " | " | —CH₂—C₆H₄—NO₂ (4-NO₂) | |
| 674 | 2,2-F₂, 1-CH₃ | C₃H₇-i | —CH₂—C₆H₃—Cl₂ (2,4-Cl₂) | |
| 675 | " | " | —CH₂—C₆H₄—CF₃ (4-CF₃) | |
| 676 | " | —C(CH₃)₂C≡CH | —CH₂—C₆H₅ | |
| 677 | " | —CH(CH₃)C≡CH | " | |
| 678 | 2-Cl, 2-F | —CH₂CH=CH₂ | —CH₂CH=CH₂ | |
| 679 | " | —CH₂C≡CH | —CH₂C≡CH | |

TABLE 1-continued
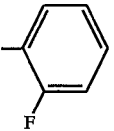
| Compound No. | $X_a$ | $R^1$ | $R^2$ | physical property |
|---|---|---|---|---|
| 680 | " | $C_3H_7$-i | 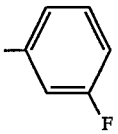 | |
| 681 | " | " | 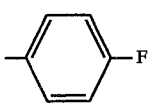 | |
| 682 | " | " | 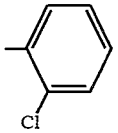 | $n_D^{20}$ 1.5155 |
| 683 | " | " | 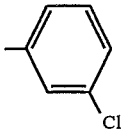 | |
| 684 | " | " | 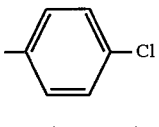 | |
| 685 | " | " | 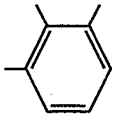 | |
| 686 | " | " | 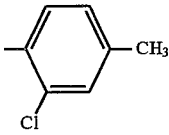 | |
| 687 | " | " | 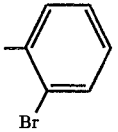 | |
| 688 | " | " | 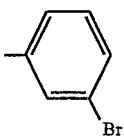 | |
| 689 | 2-Cl, 2-F | $C_3H_7$-i | | |

TABLE 1-continued $$Xn-\triangle-N(-C(=O)-)N(-N=N-)-C(=O)-NR^1R^2 \quad (I)$$

| Compound No. | $X_a$ | $R^1$ | $R^2$ | physical property |
|---|---|---|---|---|
| 690 | " | " | —C6H4—Br (4-) | |
| 691 | " | " | —C6H4—CF3 (2-) | |
| 692 | " | " | —C6H4—CF3 (3-) | |
| 693 | " | " | —C6H4—CF3 (4-) | |
| 694 | " | " | —C6H4—OCH3 (4-) | |
| 695 | " | " | —C6H4—OCHF2 (4-) | |
| 696 | " | " | —C6H4—SCF3 (4-) | |
| 697 | " | " | —C6H4—CH3 (4-) | |
| 698 | " | " | —C6H4—CH3 (3-) | |
| 699 | " | " | —C6H4—CH3 (2-) | |
| 700 | " | " | —C6H3(CH3)2 (2,5-) | |

TABLE 1-continued

Structure (I): Xn-cyclopropyl-N(H)-C(=O)-N-C(=O)-N(R¹)(R²) with tetrazole ring (N=N-N-N)

| Compound No. | $X_a$ | R¹ | R² | physical property |
|---|---|---|---|---|
| 701 | " | " | 2-($C_2H_5$)-phenyl | |
| 702 | " | " | 4-$NO_2$-phenyl | |
| 703 | " | " | 4-CN-phenyl | |
| 704 | 2,Cl, 2-F | —$(CH_2)_4$— | | |
| 705 | " | —$(CH_2)_3$—$CH(CH_3)$— | | |
| 706 | " | —$(CH_2)_2$-(2-phenyl) (fused ring) | | |
| 707 | " | —$(CH_2)_3$-(2-phenyl) (fused ring) | | |
| 708 | " | —$CH(CH_3)$—$CH_2CH_2$-(2-phenyl) (fused ring) | | mp. 65–70° C. |
| 709 | " | —$CH(CH_3)C \equiv CH$ | phenyl | |
| 710 | " | —$CH_2C \equiv CH$ | " | |
| 711 | " | $C_3H_7$-i | —$CH_2$-phenyl | |
| 712 | " | $C_3H_7$-n | phenyl | |
| 713 | " | $CH_3$ | " | |
| 714 | " | $C_2H_5$ | " | |
| 715 | " | $C_4H_9$-n | " | |
| 716 | " | $C_4H_9$-sec | " | |
| 717 | " | $C_4H_9$-i | " | |
| 718 | " | phenyl | " | |

TABLE 1-continued
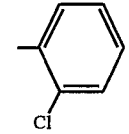
| Compound No. | $X_a$ | $R^1$ | $R^2$ | physical property |
|---|---|---|---|---|
| 719 | " | —C(CH$_3$)$_2$C≡CH | 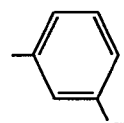 | |
| 720 | 2-Cl, 2-F | —C(CH$_3$)$_2$C≡CH | 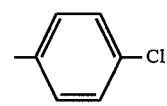 | |
| 721 | " | " | 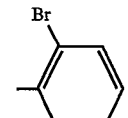 | |
| 722 | " | " | 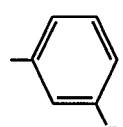 | |
| 723 | " | " | 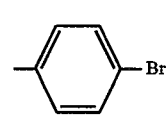 | |
| 724 | " | " |  | |
| 725 | " | " | 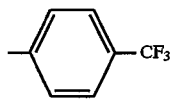 | |
| 726 | " | " |  | |
| 727 | " | " | 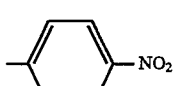 | |
| 728 | " | " | 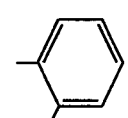 | |
| 729 | " | —CH(CH$_3$)C≡CH | | |

TABLE 1-continued structure (I): Xn-[cyclopropyl]-N(-C(=O)-)N=N-N(-C(=O)-N(R¹)(R²))

| Compound No. | $X_a$ | $R^1$ | $R^2$ | physical property |
|---|---|---|---|---|
| 730 | " | " | 3-Cl-phenyl | |
| 731 | " | " | 4-Cl-phenyl | |
| 732 | " | " | 4-CH₃-phenyl | |
| 733 | " | " | 4-Br-phenyl | |
| 734 | " | " | 3,5-diCl-phenyl | |
| 735 | 2-Cl, 2-F | —C(CH₃)₂C≡CH | 4-F-phenyl | |
| 736 | " | " | 2-F-phenyl | |
| 737 | " | —CH(CH₃)C≡CH | 4-F-phenyl | |
| 738 | " | " | 3-F-phenyl | |
| 739 | " | " | 2-F-phenyl | |
| 740 | " | $C_3H_7$-i | —CH₂(2-Cl-phenyl) | |

TABLE 1-continued
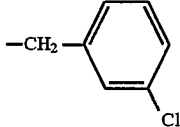
| Compound No. | $X_n$ | $R^1$ | $R^2$ | physical property |
|---|---|---|---|---|
| 741 | " | " | 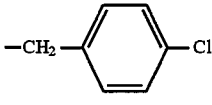 |  |
| 742 | " | " | 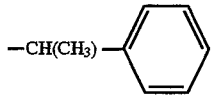 |  |
| 743 | " | " | 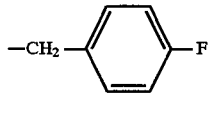 |  |
| 744 | " | " | 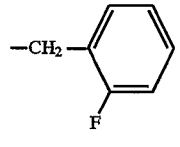 |  |
| 745 | " | " | 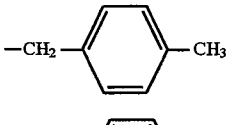 |  |
| 746 | " | " | 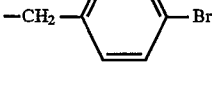 |  |
| 747 | " | " | 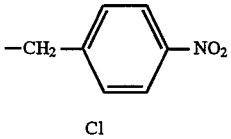 |  |
| 748 | " | " | 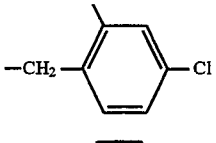 |  |
| 749 | " | " | 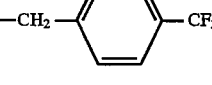 |  |
| 750 | 2,Cl, 2-F | $C_3H_7$-i | 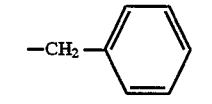 |  |
| 751 | " | —C(CH$_3$)$_2$C≡CH | —CH$_2$— phenyl |  |
| 752 | " | —CH(CH$_3$)C≡CH | " |  |
| 753 | 2-F | $C_2H_5$ | $C_2H_5$ |  |

TABLE 1-continued $$X_n-\triangleleft-\underset{N=N}{\underset{|}{N}}-\underset{\underset{N=N}{|}}{\overset{O}{\overset{\|}{C}}}-N-\overset{O}{\overset{\|}{C}}-N\overset{R^1}{\underset{R^2}{<}} \quad (I)$$

| Compound No. | $X_a$ | $R^1$ | $R^2$ | physical property |
|---|---|---|---|---|
| 754 | " | " | cyclohexyl-H | |
| 755 | " | $C_3H_7$-n | $C_3H_7$-n | |
| 756 | " | " | cyclopropyl | |
| 757 | " | " | cyclopentyl-H | |
| 758 | " | $C_3H_7$-i | phenyl | $n_D^{20}$ 1.5210 |
| 759 | " | " | cyclohexyl-H | |
| 760 | " | $-C(CH_3)_2C\equiv CH$ | phenyl | |
| 761 | " | $-CH(CH_3)C\equiv CH$ | " | |
| 762 | " | " | 4-Cl-phenyl | |
| 763 | " | " | 4-F-phenyl | |
| 764 | " | $C_3H_7$-i | 4-Cl-phenyl | |
| 765 | " | " | 4-F-phenyl | mp. 67–69° C. |
| 766 | " | $-C(CH_3)_2C\equiv CH$ | 4-Cl-phenyl | |
| 767 | " | " | 4-F-phenyl | |

TABLE 1-continued $$Xn-\triangle-N(-C(=O)-N(-C(=O)-N(R^1)(R^2)))-N=N \quad (I)$$

| Compound No. | $X_a$ | $R^1$ | $R^2$ | physical property |
|---|---|---|---|---|
| 768 | " | " | -C₆H₄-CH₃ (p) | |
| 769 | 2-F, 1-CH₃ | C₂H₅ | C₂H₅ | |
| 770 | " | " | cyclohexyl | |
| 771 | " | C₃H₇-n | C₃H₇-n | |
| 772 | " | " | cyclopropyl | |
| 773 | " | " | cyclopentyl | |
| 774 | " | C₃H₇-i | C₆H₅ | $n_D^{20}$ 1.5149 |
| 775 | " | " | cyclohexyl | |
| 776 | " | —C(CH₃)₂C≡CH | C₆H₅ | |
| 777 | " | —CH(CH₃)C≡CH | " | |
| 778 | " | " | -C₆H₄-Cl (p) | |
| 779 | " | " | -C₆H₄-F (p) | |
| 780 | " | C₃H₇-i | -C₆H₄-Cl (p) | |
| 781 | " | " | -C₆H₄-F (p) | $n_D^{20}$ 1.5103 |
| 782 | " | —C(CH₃)₂C≡CH | -C₆H₄-Cl (p) | |

TABLE 1-continued $$Xn-\triangleleft-\underset{\underset{N}{|}}{N}-\underset{\underset{\parallel}{O}}{C}-\underset{\underset{N}{|}}{N}-\underset{\underset{\parallel}{O}}{C}-N\underset{R^2}{\overset{R^1}{<}} \quad (I)$$
$$\phantom{Xn-\triangleleft-N}\underset{N}{\phantom{|}}=\underset{N}{\phantom{|}}$$

| Compound No. | $X_a$ | $R^1$ | $R^2$ | physical property |
|---|---|---|---|---|
| 783 | " | " | 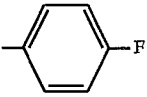 | |
| 784 | " | " | 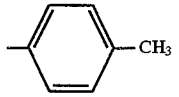 | |
| 785 | — | —C(CH$_3$)$_2$—CH=CH— 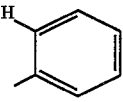 | | $n_D^{20}$ 1.5749 |
| 786 | — | —C(CH$_3$)$_2$—CH=CH— 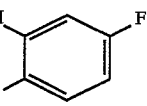 | | $n_D^{20}$ 1.5602 |
| 787 | — | C$_3$H$_7$-i | CH$_3$ | |
| 788 | — | " | C$_2$H$_5$ | $n_D^{20}$ 1.4938 |
| 789 | 2,2-Cl$_2$ | " | CH$_3$ | |
| 790 | " | " | C$_2$H$_5$ | |
| 791 | 2,2-F$_2$, 1-CH$_3$ | " | CH$_3$ | |
| 792 | " | " | C$_2$H$_5$ | $n_D^{20}$ 1.4655 |
| 793 | 2,2-F$_2$ | " | CH$_3$ | |
| 794 | " | " | C$_2$H$_5$ | $n_D^{20}$ 1.4670 |
| 795 | 1-CH$_3$ | " | " | |
| 796 | 2-CH$_3$ | " | " | |
| 797 | 2,2-Cl$_2$, 1-CH$_3$ | " | CH$_3$ | |
| 798 | — | 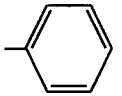 |  | |
| 799 | 2,2-Cl$_2$, 1,2-(CH$_3$)$_2$ | C$_3$H$_7$-i | CH$_3$ | |
| 800 | " | " | C$_2$H$_5$ | |
| 801 | 1-Cl | " | 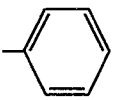 | $n_D^{20}$ 1.5318 |
| 802 | — | " | —CH$_2$CH=CH$_2$ | |
| 803 | 2,2-F$_2$ | " | " | |
| 804 | 2,2-F$_2$, 1-CH$_3$ | —CH$_2$CH=CH$_2$ | " | |
| 805 | — |  |  | |
| 806 | 2-F, 1-CH$_3$ | C$_3$H$_7$-i | C$_2$H$_5$ | |
| 807 | 2-F | " | " | |
| 808 | 2-Cl, 2-F | " | " | $n_D^{20}$ 1.4821 |
| 809 | — | —CH(CH$_3$)—(CH$_2$)$_3$—CH(CH$_3$)— | " | mp. 109~112° C. |
| 810 | 1-CH$_3$ | " | " | |
| 811 | 2-CH$_3$ | " | " | |
| 812 | 2,2-F$_2$ | " | " | |
| 813 | — | —CH(CH$_3$)—(CH$_2$)$_2$—CH(CH$_3$)— | " | |
| 814 | 1-CH$_3$ | " | " | |
| 815 | 2-CH$_3$ | " | " | |
| 816 | 2-F | " | " | |

TABLE 1-continued (Structure I: Xn-cyclopropyl-N-N(=O)C-N(=O)C-N(R¹)(R²) with tetrazole ring)

| Compound No. | $X_a$ | R¹ | R² | physical property |
|---|---|---|---|---|
| 817 | — | —CH(CH₃)CH₂—(phenyl) | | mp. 134~135° C. |
| 818 | 1-CH₃ | " | | |
| 819 | 2-CH₃ | " | | |
| 820 | — | —CH(CH₃)CH(CH₃)—(2-methylphenyl) | | |
| 821 | — | —C(CH₃)=CH—(2-methylphenyl) | | $n_D^{20}$ 1.5928 |
| 822 | 1-CH₃ | " | | |
| 823 | 2-CH₃ | " | | |
| 824 | 2,2-F₂, 1-CH₃ | " | | |
| 825 | — | —CH(CH₂)CH₂CH₂—(2-methyl-5-fluorophenyl) | | mp. 130~131° C. |
| 826 | 1-CH₃ | " | | |
| 827 | 2-CH₃ | " | | |
| 828 | 2,2-F₂ | " | | |
| 829 | 2,2-F₂, 1-CH₃ | " | | |
| 830 | 2-F | —CH(CH₃)CH₂CH₂—(2-methylphenyl) | | $n_D^{20}$ 1.5444 |
| 831 | 2-F₂, 1-CH₃ | " | | mp. 91~96° C. |
| 832 | — | —CH(CH(CH₃)₂)CH₂CH₂—(2-methylphenyl) | | |
| 833 | — | —CH(CH₃)CH₂CH₂—(2-methyl-5-methylphenyl) | | mp. 116~118° C. |
| 834 | — | —CH(CH₃)CH₂CH₂—(2-methyl-5-chlorophenyl) | | |

TABLE 1-continued $$X_n-\triangle-\underset{\underset{N}{|}}{N}-\underset{\underset{\|}{O}}{C}-\underset{\underset{N}{|}}{N}-\underset{\underset{\|}{O}}{C}-N\underset{R^2}{\overset{R^1}{<}} \quad (I)$$

| Compound No. | $X_a$ | $R^1$ | $R^2$ | physical property |
|---|---|---|---|---|
| 835 | — | —CH(CH$_3$)CH$_2$CH$_2$— | 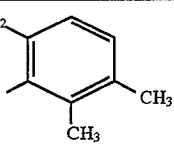 | |
| 836 | — | —CH(CH$_3$)CH$_2$CH$_2$— | 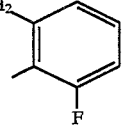 | |
| 837 | — | —CH(CH$_3$)CH$_2$CH$_2$— | 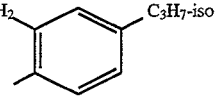 | |
| 838 | — | —CH(CH$_3$)CH$_2$CH(CH$_2$)— | 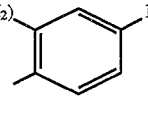 | |
| 839 | — | —C(CH$_3$)$_2$CH$_2$CH$_2$— | 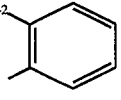 | $n_D^{20}$ 1.5515 |
| 840 | 1-CH$_3$ | " | | mp. 86–89° C. |
| 841 | 2-CH$_3$ | " | | $n_D^{20}$ 1.5498 |
| 842 | 2,2-F$_2$ | " | | |
| 843 | 2,2-F$_2$, 1-CH$_3$ | " | | |
| 844 | 2,2-(CH$_3$)$_2$ | " | | |
| 845 | 2,2-Cl$_2$ | " | | |
| 846 | 2-Cl, 2-F | " | | |
| 847 | — | —C(CH$_3$)$_2$CH$_2$CH$_2$— | 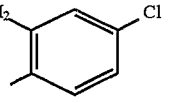 | |
| 848 | — | —C(CH$_3$)$_2$CH$_2$CH$_2$— | 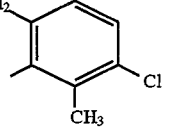 | |
| 849 | — | —C(CH$_3$)$_2$CH$_2$CH(CH$_3$)— | 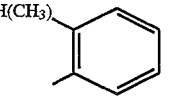 | $n_D^{20}$ 1.5450 |
| 850 | — | —C(CH$_3$)$_2$CH$_2$CH(CH$_3$)— | 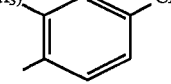 | mp. 117.5–120.5° C. |

TABLE 1-continued $$\text{Xn} \longrightarrow \triangle \text{—N(C(=O))—N—C(=O)—N(R}^1\text{)(R}^2\text{)} \quad \text{with N=N ring} \quad (I)$$

| Compound No. | $X_A$ | $R^1$ | $R^2$ | physical property |
|---|---|---|---|---|
| 851 | 1-CH$_3$ | —C(CH$_3$)$_2$CH=CH— | 2-methylphenyl | mp. 94.5–96.5° C. |
| 852 | 2-CH$_3$ | —C(CH$_3$)$_2$CH=CH— | 2,5-dimethylphenyl | $n_D^{20}$ 1.5549 |
| 853 | 2,2-F$_2$ | " | | |
| 854 | 2,2-F$_2$, 1-CH$_3$ | " | | $n_D^{20}$ 1.5254 |
| 855 | 2-Cl, 2-F | " | | |
| 856 | 2-F | " | | |
| 857 | 2-F, 1-CH$_3$ | " | | |
| 858 | — | —C(CH$_3$)$_2$CH=CH— | 5-bromo-2-methylphenyl | |
| 859 | — | —C(CH$_3$)$_2$CH=CH— | 2,3,4-trimethylphenyl | $n_D^{20}$ 1.5568 |
| 860 | 2,2-F$_2$, 1-CH$_3$ | " | | |
| 861 | — | —C(CH$_3$)$_2$CH=CH— | 2,5-dimethylphenyl | |
| 862 | 1-CH$_3$ | —C(CH$_3$)$_2$CH=CH— | 5-fluoro-2-methylphenyl | |
| 863 | 2-CH$_3$ | " | | |
| 864 | — | —C(CH$_3$)$_2$CH=CH— | 5-chloro-2-methylphenyl | mp. 111–113.5° C. |
| 865 | — | —C(CH$_3$)$_2$CH=CH— | 5-isopropyl-2-methylphenyl | |
| 866 | — | —C(CH$_3$)$_2$CH=CH— | 2-methyl-4-(CH$_2$CH$_3$)phenyl | |

TABLE 1-continued $$Xn \!-\!\!\triangleright\!\!-\!\!\underset{\underset{N\,=\!=\!=\!N}{|}}{N}\!\!-\!\!\overset{\overset{O}{\|}}{C}\!\!-\!\!N\!\!-\!\!\overset{\overset{O}{\|}}{C}\!\!-\!\!N\!\!\overset{R^1}{\underset{R^2}{}} \qquad (I)$$

| Compound No. | X$_a$ | R$^1$ | R$^2$ | physical property |
|---|---|---|---|---|
| 867 | — | —C(CH$_3$)$_2$CH=CH— | 2,3-dimethylphenyl | |
| 868 | — | —C(CH$_3$)$_2$CH=CH— | 3,4-dichlorophenyl | |
| 869 | — | —C(CH$_3$)$_2$CH=C(CH$_3$)— | phenyl | n$_D^{20}$ 1.5603 |
| 870 | — | —C(CH$_3$)$_2$CH=C(CH$_3$)— | 3-methylphenyl | |
| 871 | — | —C(CH$_3$)$_2$CH=C(CH$_3$)— | 3-fluorophenyl | |
| 872 | — | —C(CH$_3$)$_2$CH=CH(CH$_3$)— | 3-chlorophenyl | |
| 873 | 2,2-F$_2$, 1-CH$_3$ | —C(CH$_3$)$_2$CH=C(CH$_3$)— | 3-fluorophenyl | |

Synthesis Example 2

(Synthesis of an intermediate)

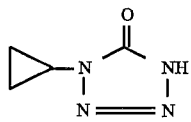

Cyclopropyl isocyanate (10 g), trimethylsilyl azide (20.8 g) and a catalytic amount of boron trifluoride ethyl etherate are mixed and heated for 40 hours with refluxing. The excess trimethylsilyl azide is distilled off under reduced pressure, methanol is added to the residue and then methanol is distilled off under reduced pressure. Purifying the residue by column chromatography (eluent:ethanol/chloroform=6/100) gives cyclopropyl-5(4H)-tetrazolinone (12.0 g). m.p. 100°–104° C.

Synthesis Example 3

(Synthesis of an intermediate)

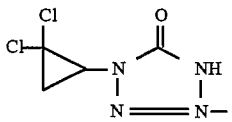

2,2-Dichlorocyclopropanecarbonyl chloride (10 g), trimethylsilyl azide (20.0 g) and a catalytic amount of boron trifluoride ethyl etherate are mixed and heated for 48 hours with refluxing. The excess trimethylsilyl azides is distilled off under reduced pressure, methanol is added to the residue and then methanol is distilled off under reduced pressure. Purifying the residue by column chromatography (eluent:ethanol/chloroform=6/100 gives 1-(2,2-dichlorocyclopropyl)-5(4H)-tetrazolinone (8.5 g). m.p. 109°–112° C.

The compounds obtained in the foregoing Synthesis Examples 2 and 3 along with additional compounds of formula (II), obtainable by a method corresponding to that used in the above Synthesis Examples 2 and 3, are shown in the following Table 2.

TABLE 2

$$\text{Xn} \triangleright \text{N}(-\text{C}(=\text{O})-\text{NH}-\text{N}=\text{N}) \quad (II)$$

| Compound No. | $X_a$ | physical property |
|---|---|---|
| 2.1 | — | mp. 100~104° C. |
| 2.2 | 2-CH$_3$ | $n_D^{20}$ 1.4906 |
| 2.3 | 1-CH$_3$ | $n_D^{20}$ 1.4634 |
| 2.4 | 2,2-(CH$_3$)$_2$ | |
| 2.5 | 2,3-(CH$_3$)$_2$ | |
| 2.6 | 1,2-(CH$_3$)$_2$ | |
| 2.7 | 1,2,2-(CH$_3$)$_3$ | |
| 2.8 | 1,2,3-(CH$_3$)$_3$ | |
| 2.9 | 2,2,3,3-(CH$_3$)$_4$ | mp. 110~112° C. |
| 2.10 | 1-C$_2$H$_5$ | |
| 2.11 | 2-C$_2$H$_5$ | |
| 2.12 | 1-C$_2$H$_5$, 2-CH$_3$ | |
| 2.13 | 2-C$_2$H$_5$, 3-CH$_3$ | |
| 2.14 | 2-C$_3$H$_7$-n | |
| 2.15 | 2-C$_3$H$_7$-i | |
| 2.16 | 1-C$_3$H$_7$-i | |
| 2.17 | 2,2-(CH$_3$)$_2$, 1-CH=CH$_2$ | |
| 2.18 | 2,2-(CH$_3$)$_2$, 1-CH=C(CH$_3$)$_2$ | mp. 99~102° C. |
| 2.19 | 2,2-Cl$_2$ | mp. 109~112° C. |
| 2.20 | 2,2-Br$_2$ | |
| 2.21 | 2,2-F$_2$ | $n_D^{20}$ 1.4443 |
| 2.22 | 2-Cl, 2-F | $n_D^{20}$ 1.4761 |
| 2.23 | 2-Cl, 2-F, 1-CH$_3$ | |
| 2.24 | 2,2-Br$_2$, 1-CH$_3$ | |
| 2.25 | 2,2-Br$_2$, 1,3-(CH$_3$)$_2$ | |
| 2.26 | 2,2-Cl$_2$, 1-CH$_3$ | mp. 129~132° C. |
| 2.27 | 2,2-Cl$_2$, 1,3-(CH$_3$)$_2$ | |
| 2.28 | 2,2-F$_2$, 1-CH$_3$ | mp. 75~78.5° C. |
| 2.29 | 2,2-Cl$_2$, 3-CH$_3$ | |
| 2.30 | 2,2-Cl$_2$, 1,3,3-(CH$_3$)$_3$ | mp. 100~104° C. |
| 2.31 | 2,2-Cl$_2$, 1-C$_2$H$_5$ | |
| 2.32 | 2,2-Cl$_2$, 1-C$_2$H$_5$, 3-CH$_3$ | |
| 2.33 | 2,2-Cl$_2$, 1-C$_3$H$_7$-i | |
| 2.34 | 2-F | $n_D^{20}$ 1.4778 |
| 2.35 | 2-F, 1-CH$_3$ | mp. 128~131° C. |
| 2.36 | 1-Cl | mp. 55~58° C. |

Test Example 1

Pre-emergence soil treatment test against plowed land weeds

Method of preparation:
carrier: acetone, 5 parts by weight
emulsifying agent; benzyloxypolyglycol ether, 1 part by weight An emulsion is obtained by mixing 1 part by weight of the active compound with the above amounts of carrier and emulsifying agent. A portion of this emulsion containing a prescribed amount of the chemical is diluted with water to prepare the formulation for testing.

Testing Method:

In the greenhouse, seeds of Echinochloa and *Amaranthus lividus* were sowed in the surface layer of plowed land soil filled in a 120 cm$^2$ pot with soil-covering and the above formulated in a 120 cm$^2$ pot with soil-covering and the above formulated chemical was uniformly spread on the surface layer of soil in the test pot in prescribed amount of the chemical. 4 weeks after spreading, the herbicidal effect was examined. The herbicidal effect was rated as 100% for complete death and as 0% for untreated pots.

Result:

The weeds were 100% killed by application of 1 kg/ha of compounds Nos. 1, 2, 8, 12, 13, 14, 31, 46, 50, 51, 63, 102, 177, 488 and 492.

Test Example 2

Post-emergence foliage treatment test against plowed land weeds

Testing Method:

In the greenhouse, seeds of Echinochloa and *Amaranthus lividus* were sowed in a 120 cm$^2$ pot filled with plowed land soil and covered with soil. 10 Days after sowing (when the weeds on average in the a-leaf stage, the formulated chemical prepared similarly to foregoing Test Example 1 was uniformly spread on the foliage of the test plant in each test pot in prescribed amount. 3 weeks after spreading the herbicidal effect was examined.

Result:

90% or more of the weeds were killed by application of 2 kg/ha of Compounds Nos. 8, 12, 13, 31, 46, 63, 102, 177 and 492.

Formulation Example 1

(granules)

Twenty-five parts of water are added to a mixture of 10 parts of Compound No. 8, 30 parts of bentonite (montmorillonite), 58 parts of talc and 2 parts of lignin sulphonic acid salt to be well kneaded followed by granulating to 10–40 mesh granules using an extrusion type granulation and drying at 40°–50° C.

Formulation Example 2

(granules)

A rotary mixer is charged with 95 parts of clay mineral granules having a particle size distribution within the range of 0.2–2 mm and 5 parts of Compound No. 102 is sprayed therein with a liquid diluent under continuous rotation for uniformly wetting, followed by drying at 40°–50° C.

Formulation Example 4

(granules)

An emulsion is obtained by mixing and stirring 30 parts of Compound No. 8, 55 parts of xylene, 8 parts of polyoxyethelene alkylphenyl ether and 7 parts of calcium alkylbenzene sulphonate.

Formulation Example 4

(wettable powder)

A wettable powder is obtained by grinding and mixing 15 parts of Compound No. 31, 80 parts of a mixture of White Carbon (fine powder of hydrated non-crystalline silicon oxide) and powdery clay (1:5), 2 parts of sodium alkylbenzene sulphonate and 3 parts of a condensate of sodium alkylnaphthalene sulphonate with formaldehyde.

Formulation Example 5

(wettable granules)

Twenty parts of Compound No. 46, 30 parts of sodium lignin sulphonate, 15 parts of bentonite and 35 parts of calcined diatomaceous earth powder are mixed and water is added to the mixture followed by extrusion through a 0.3 mm screen and drying to give wettable granules.

It will be understood that the specification and examples are illustrative but not limitative of the present invention and that other embodiment within the spirit and scope of the invention will suggest themselves to those skilled in the art.

We claim:

1. A 1-cyclopropyl tetrazolinone of the formula

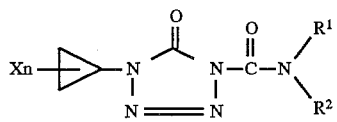

wherein

X represent $C_{1-3}$ alkyl, $C_{2-4}$ alkenyl or halogen, n represent 0 to 5, $R^1$ and $R^2$ each independently represents $C_{1-6}$-alkyl, $C_{2-6}$ alkenyl, $C_{2-6}$ alkynyl, $C_{3-7}$ cycloalkyl which may optionally be substituted by $C_{1-3}$ alkyl, epoxy-$C_{3-5}$ alkan-1-yl, optionally substituted phenyl, optionally substituted benzyl, optionally substituted 1-phenylethyl and optionally substituted 2-phenylethyl wherein the substituents are selected from the group consisting of halogen, $C_{1-4}$ alkyl, $C_{1-4}$ alkoxy, $C_{1-4}$ haloalkyl, $C_{1-4}$ haloalkoxy, $C_{1-4}$ alkylthio, $C_{1-4}$ haloalkylthio, cyano, nitro, $C_{1-4}$ alkylcarbonyl, $C_{1-4}$ alkoxycarbonyl, and alkoxyimino-$C_{1-2}$-alkyl, or $R^1$ and $R^2$ together with the N-atom to which they are attached, represent an optionally methyl or ethyl substituted cyclic ring wherein said ring is selected from the group consisting of pyrrolidin-1-yl, indol-1-yl, indolin-1-yl, 1,2-dihydroquinolin-1-yl, and 1,2,3,4-tetrahydroquinolin 1-yl.

2. A compound according to claim 1, wherein

X represents methyl, ethyl, vinyl, allyl, 1-propenyl, fluorine, chlorine, or bromine, n represents 0 to 4, and $R^1$ and $R^2$ each independently represents $C_{1-4}$ alkyl, $C_{3-5}$ alkenyl, $C_{3-5}$ alkynyl, $C_{3-6}$ cycloalkyl which may optionally be substituted by methyl, 2,3-epoxypropan-1-yl, phenyl which may optionally be substituted or benzyl which may optionally be substituted, the optional substituents on said phenyl or said benzyl being independently selected from the group consisting of halogen, $C_{1-4}$ alkyl, $C_{1-4}$ alkoxy, $C_{1-2}$ haloalkyl, $C_{1-2}$ haloalkoxy, $C_{1-4}$ alkylthio, $C_{1-2}$ haloalkylthio, cyano, nitro, $C_{1-2}$ alkylcarbonyl and $C_{1-2}$ alkoxyimino-$C_{1-2}$ alkyl, or $R^1$ and $R^2$ together with the N-atom to which they are attached, represent pyrrolidin-1-yl, indol-1-yl, indolin-1-yl, 1,2-dihydroquinolin-1-yl or 1,2,3,4-tetrahydroquinolin-1-yl which may optionally be substituted by methyl.

3. A compound according to claim 1, wherein

X represents methyl, ethyl, fluorine or chlorine, n represents 0 to 4, and $R^1$ and $R^2$ each independently represents $C_{1-3}$ alkyl, $C_{3-5}$ alkyl, $C_{3-5}$ alkynyl, cyclopropyl, cyclopentyl, cyclohexyl which may optionally be substituted by methyl, 2,3-epoxypropan-1-yl, phenyl which may optionally be substituted or benzyl which may optionally be substituted the optional substituents on said phenyl or said benzyl being independently selected from the group consisting of fluorine, chlorine, bromine, methyl, ethyl, methoxy, ethoxy, difluoromethyl, trifluoromethyl, difluoromethoxy, trifluoromethoxy, methylthio, ethylthio, trifluoromethylthio, cyano, nitro, acetyl, propionyl and 1-methoxyiminoethyl, or $R^1$ and $R^2$ together with N-atom to which they are attached, represent pyrrolidin-1-yl, indol-1-yl, indolin-1-yl, 1,2-dihydroquinolin-1-yl, or 1,2,3,4-tetrahydroquinolin-1-yl which may optionally be substituted by methyl.

4. A herbicidal composition comprising a herbicidally effective amount of a compound according to claim 1, and a diluent.

5. A method of combatting unwanted vegetation which comprises applying to such vegetation or to a locus from which it is desired to exclude such vegetation a herbicidally effective amount of a compound according to claim 1.

6. A compound of the formula

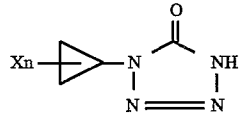

wherein

X represents $C_{1-3}$ alkyl, $C_{2-4}$ alkenyl or halogen, and n' represent 1 to 5.

* * * * *

UNITED STATES PATENT AND TRADEMARK OFFICE
CERTIFICATE OF CORRECTION

PATENT NO. : 5,650,374
DATED : July 22, 1997
INVENTOR(S) : Goto, et al.

It is certified that error appears in the above-indentified patent and that said Letters Patent is hereby corrected as shown below:

Col. 144, lines 7-8     Delete " $C_{3-5}$alkyl, " and substitute -- $C_{3-5}$akenyl, --

Col. 144, line 35       Delete formula and substitute

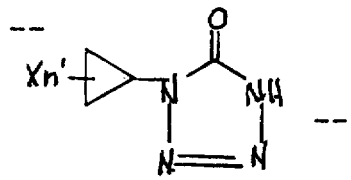

--

Signed and Sealed this

Sixteenth Day of December, 1997

Attest:

BRUCE LEHMAN

Attesting Officer

Commissioner of Patents and Trademarks